(12) United States Patent
Salas Pérez-Rasilla et al.

(10) Patent No.: US 9,957,565 B2
(45) Date of Patent: May 1, 2018

(54) METHOD FOR DETECTING POLYMORPHISMS

(75) Inventors: Eduardo Salas Pérez-Rasilla, Barcelona (ES); Jaume Marrugat De La Iglesia, Barcelona (ES); Roberto Elosua Llanos, Barcelona (ES); Sergio Castillo Fernandez, Barcelona (ES); Joan Salgado Gómez, Barcelona (ES); Jose Maria Ordovás Munoz, Barcelona (ES)

(73) Assignee: Gendiag.exe, S.L., Barcelona (ES)

( * ) Notice: Subject to any disclaimer, the term of this patent is extended or adjusted under 35 U.S.C. 154(b) by 0 days. days.

(21) Appl. No.: 13/377,216

(22) PCT Filed: Jun. 9, 2010

(86) PCT No.: PCT/EP2010/058064
§ 371 (c)(1),
(2), (4) Date: Feb. 22, 2012

(87) PCT Pub. No.: WO2010/142713
PCT Pub. Date: Dec. 16, 2010

(65) Prior Publication Data
US 2012/0141450 A1 Jun. 7, 2012

(30) Foreign Application Priority Data
Jun. 9, 2009 (EP) .................................... 09162329

(51) Int. Cl.
*C12Q 1/68* (2018.01)
(52) U.S. Cl.
CPC ..... *C12Q 1/6883* (2013.01); *C12Q 2600/156* (2013.01)
(58) Field of Classification Search
None
See application file for complete search history.

(56) References Cited

U.S. PATENT DOCUMENTS

2007/0015170 A1* 1/2007 Salonen et al. .................. 435/6
2008/0274460 A1 11/2008 Cohen
2008/0274471 A1 11/2008 Cohen et al.

FOREIGN PATENT DOCUMENTS

| EP | 09162329 | 9/2009 |
| EP | 09162329 | 6/2011 |
| RU | 2322193 C1 | 4/2008 |
| WO | WO 2008/102380 | 8/2008 |
| WO | PCT/EP2010/058064 | 12/2011 |

OTHER PUBLICATIONS

Schunkert et al. (Circulation. 2008;117:1675-1684).*
Samani et al. (N Engl J Med 357;5: 443-453).*
Myocardial Infarction Genetics Consortium, (Nature Genetics, Mar. 2009;41(3):334-41, Epub date: Feb. 8, 2009),.*
Erdmann et al. (Nature Genetics; Mar. 2009;41(3):280-2; Epub date: Feb. 8, 2009.).*
NCBI (dbSNP database search results, pp. 1-11).*
Erdmann et al., New susceptibility locus for coronary artery disease on chromosome 3q22.3. Nat Genet. Mar. 2009;41(3):280-2. doi: 10.1038/ng.307. Epub Feb. 8, 2009.
Kathiresan et al., Genome-wide association of early-onset myocardial infarction with single nucleotide polymorphisms and copy numbers variants. Nat Genet. Mar. 2009;41(3):334-41. Epub Feb. 8, 2009.
Schunkert et al., Repeated replication and a prospective meta-analysis of the association between chromosome 9p21.3 and coronary artery disease. Circulation, 117(3):1675-1684 (2008).
Karvanen et al., The impact of newly identified loci on coronary heart disease, stroke and total mortality in the MORGAM prospective cohorts. Genetic Epidemiology, 33(3):237-246 (2009).
Samani et al., Genome wide association analysis of coronary artery disease. The New England Journal of Medicine, 357(5):443-453 (2007).
Ye et al., Association of genetic variation on chromosome 9p21 with susceptibility and progression of atherosclerosis: a population-based, prospective study. Journal of the American College of Cardiology, 52(5):378-384 (2008).
Wellcome Trust Case Control Consortium, Genome wide association study of 14,000 cases of seven common diseases and 3,000 shared controls. Nature, 447(7145): 661-678 (2007).
Dehghan et al., Lack of association of two common polymorphisms on 9p21 with risk of coronary heart disease and myocardial infarction; results from a prospective cohort study. BMC Medicine, 6(30):1-7 (2008).
Yamada et al., Molecular genetics of myocardial infarction. Genomic Medicine, 2(1-2):7-22 (2008).
Lluís-Ganella et al., Additive effects of multiple genetic variants on the risk of coronary artery disease. Rev Esp Cardiol. Aug. 2010;63(8):925-33.
Lluis-Ganella et al., Assessment of the value of a genetic risk score in improving the estimation of coronary risk. Atherosclerosis. Jun. 2012;222(2):456-63. doi: 10.1016/j.atherosclerosis.2012.03.024. Epub Mar. 30, 2012.
[No Author Listed], GeneChip TM Human Mapping 500K Array Set. 2006.
Levy et al., Genome-wide association study of blood pressure and hypertension. Nat Genet. Jun. 2009;41(6):677-87. doi: 10.1038/ng. 384. Epub May 10, 2009.
Bangalore et al., Cardiovascular protection using beta-blockers: a critical review of the evidence. J Am Coll Cardiol. Aug. 14, 2007;50(7):563-72. Epub Jul. 30, 2007.
[No Author Listed] Genechip® Human Mapping 500K Array Set. Affymetrix. 2007. 1-4.

(Continued)

*Primary Examiner* — Pablo S Whaley
(74) *Attorney, Agent, or Firm* — Wolf, Greenfield & Sacks, P.C.

(57) ABSTRACT

The invention relates to a method for determining the risk of suffering a cardiovascular disease based on the presence of different polymorphisms as well as to kits for practicing the above method. The invention also relates to a method for determining the risk of suffering a cardiovascular disease by combining the absence or presence of one or more polymorphic markers in a sample from the subject with conventional risk factors for CVD as well as computer-implemented means for carrying out said method.

6 Claims, 4 Drawing Sheets

(56) References Cited

OTHER PUBLICATIONS

Figure 1:
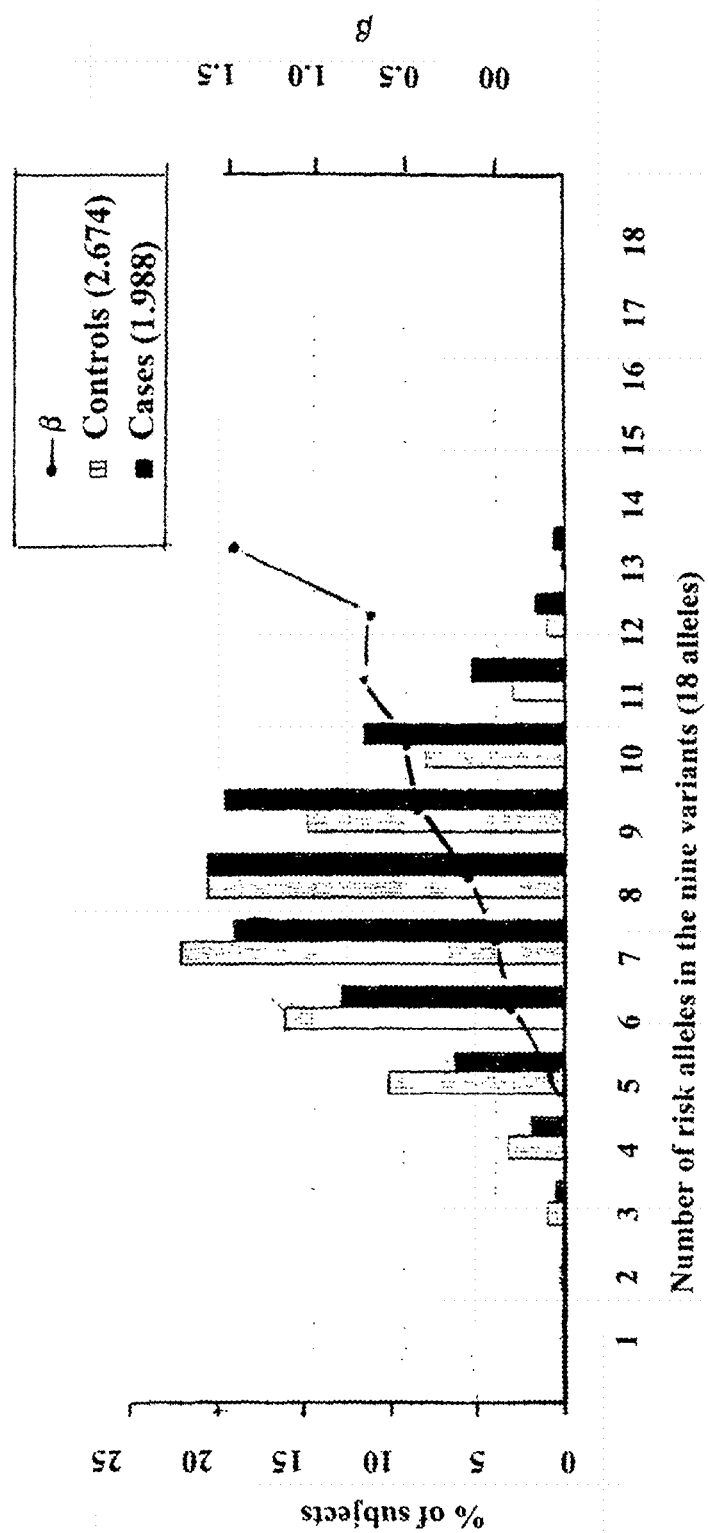

Iribarren et al., Clinical Utility of Multimarker Genetic Risk Scores for Prediction of Incident Coronary Heart Disease: A Cohort Study Among Over 51 Thousand Individuals of European Ancestry. Circ Cardiovasc Genet. Dec. 2016;9(6):531-540. doi: 10.1161/CIRCGENETICS.116.001522.

Thanassoulis et al., A genetic risk score is associated with incident cardiovascular disease and coronary artery calcium: the Framingham Heart Study. Circ Cardiovasc Genet. Feb. 1, 2012;5(1):113-21. doi:10.1161/CIRCGENETICS.111.961342.

* cited by examiner

Figure 2

| Alleles | Number of Controls | Number of Cases | OR [95%CI] | β | Δβ | p value |
|---|---|---|---|---|---|---|
| 1 | 1 | 1 | 3,13 [0,04-245,35] | 1,141 | 1,603 | 4 x 10$^{-01}$ |
| 2 | 5 | 1 | 0,63 [0,01-5,62] | -0,462 | 0,102 | 1 x 10$^{-01}$ |
| 3 | 48 | 8 | 0,52 [0,21-1,13] | -0,654 | -0,798 | 1 x 10$^{-01}$ |
| 4 | 171 | 38 | 0,70 [0,47-1,01] | -0,356 | -0,042 | 5 x 10$^{-02}$ |
| 5 | 540 | 127 | 0,74 [0,58-0,93] | -0,314 | -0,231 | 7 x 10$^{-03}$ |
| 6 | 862 | 254 | 0,92 [0,77-1,11] | -0,083 | -0,083 | 4 x 10$^{-01}$ |
| 7 | 1186 | 379 | 1,00 | 0 | 0 | 1 |
| 8 | 1103 | 410 | 1,16 [0,99-1,37] | 0,148 | 0,148 | 7 x 10$^{-02}$ |
| 9 | 791 | 389 | 1,54 [1,30-1,83] | 0,437 | 0,284 | 5 x 10$^{-07}$ |
| 10 | 435 | 230 | 1,65 [1,35-2,02] | 0,501 | 0,069 | 7 x 10$^{-07}$ |
| 11 | 160 | 107 | 2,09 [1,59-2,76] | 0,737 | 0,236 | 2 x 10$^{-07}$ |
| 12 | 50 | 32 | 2,00 [1,22-3,23] | 0,693 | -0,044 | 4 x 10$^{-03}$ |
| 13 | 8 | 11 | 4,30 [1,56-12,41] | 1,458 | 0,765 | 2 x 10$^{-02}$ |
| 14 | 1 | 1 | 3,13 [0,04-245,35] | 1,141 | -0,317 | 4 x 10$^{-01}$ |

Reference group → (row 7)

Figure 4

| Quintile | Alleles | Number of controls | Number of cases | OR [95% CI] | β | Δβ | p value |
|---|---|---|---|---|---|---|---|
| $Q_1$ | 1-6 | 1627 | 429 | 1 | 0 | 0 | - |
| $Q_2$ | 7 | 1186 | 379 | 1,21 [1,04-1,42] | 0,191 | 0,191 | $1,6 \times 10^{-02}$ |
| $Q_3$ | 8 | 1103 | 410 | 1,41 [1,21-1,65] | 0,344 | 0,153 | $1,5 \times 10^{-05}$ |
| $Q_4$ | 9 | 791 | 389 | 1,87 [1,59-2,18] | 0,626 | 0,282 | $3,7 \times 10^{-14}$ |
| $Q_5$ | 10-14 | 654 | 381 | 2,21 [1,87-2,61] | 0,793 | 0,167 | $5,0 \times 10^{-21}$ |

SEQUENCE LISTING

```
<160> NUMBER OF SEQ ID NOS: 15

<210> SEQ ID NO 1
<211> LENGTH: 52
<212> TYPE: DNA
<213> ORGANISM: Homo sapiens

<400> SEQUENCE: 1
tcatactaac catatgatca acagttcaaa agcagccact cgcagaggta ag          52

<210> SEQ ID NO 2
<211> LENGTH: 52
<212> TYPE: DNA
<213> ORGANISM: Homo sapiens

<400> SEQUENCE: 2
aaagagaaag aaataggagc aggatcaact tccagatata cagagaatat aa          52

<210> SEQ ID NO 3
<211> LENGTH: 52
<212> TYPE: DNA
<213> ORGANISM: Homo sapiens

<400> SEQUENCE: 3
aaccataata gttatgctga gaagttctttt tttgtcatag tgcaagataa ca         52

<210> SEQ ID NO 4
<211> LENGTH: 52
<212> TYPE: DNA
<213> ORGANISM: Homo sapiens

<400> SEQUENCE: 4
```
ttgaaaaaaa ttaattctca cactcctaag tgcatttaat ttaagctact tt        52

<210> SEQ ID NO 5
<211> LENGTH: 52
<212> TYPE: DNA
<213> ORGANISM: Homo sapiens

<400> SEQUENCE: 5
aaaagcaagc acatctgtgg cattaccaac attaaatatt tatatacata gt        52

<210> SEQ ID NO 6
<211> LENGTH: 52
<212> TYPE: DNA
<213> ORGANISM: Homo sapiens

<400> SEQUENCE: 6
acagttttta ctgtaactgc aataaataa tactcatctt taaaaagaca tc         52

<210> SEQ ID NO 7
<211> LENGTH: 52
<212> TYPE: DNA
<213> ORGANISM: Homo sapiens

<400> SEQUENCE: 7
ggcaagtacc tgggcacagg gctgcttcat ggccttggac ctggacagtg ga        52

<210> SEQ ID NO 8
<211> LENGTH: 52
<212> TYPE: DNA
<213> ORGANISM: Homo sapiens

<400> SEQUENCE: 8
acatctgcct ctctagacta taaactcttt ggggctaggt cttctttgtc tt        52

<210> SEQ ID NO 9
<211> LENGTH: 52
<212> TYPE: DNA
<213> ORGANISM: Homo sapiens

<400> SEQUENCE: 9
gctatcattt aaatttggtt gagacacaat atgctgttgc actttctata aa        52

<210> SEQ ID NO 10
<211> LENGTH: 52
<212> TYPE: DNA
<213> ORGANISM: Homo sapiens

<400> SEQUENCE: 10
ctgtgctgct tggtgcctct ctgatatgaa tacactgaca cgtcaaagta ac        52

<210> SEQ ID NO 11
<211> LENGTH: 52
<212> TYPE: DNA
<213> ORGANISM: Homo sapiens

<400> SEQUENCE: 11
cttgctccag catccaggag gtccggtggt gcacacggct tgagatgcct ga        52

<210> SEQ ID NO 12
<211> LENGTH: 61
<212> TYPE: DNA
<213> ORGANISM: Homo sapiens

```
<400> SEQUENCE: 12
agatcacact gtctttgccg tcattgaact cgcaacctaa ctgctgagtg aggacacgtc    60
c                                                                    61

<210> SEQ ID NO 13
<211> LENGTH: 52
<212> TYPE: DNA
<213> ORGANISM: Homo sapiens

<400> SEQUENCE: 13
gaagggtaaa gggtggtagg attgagtgag tcaggccaga aacctctagt ta            52

<210> SEQ ID NO 14
<211> LENGTH: 52
<212> TYPE: DNA
<213> ORGANISM: Homo sapiens

<400> SEQUENCE: 14
aggacaatgc tcaccctctt tgcaccgcta tcacatcacc tgttcagggc ac            52

<210> SEQ ID NO 15
<211> LENGTH: 52
<212> TYPE: DNA
<213> ORGANISM: Homo sapiens

<400> SEQUENCE: 15
tacaggattc aacaattagt caaaaagtca tgagctaaca aaataggagc tt            52
```

METHOD FOR DETECTING POLYMORPHISMS

RELATED APPLICATIONS

This application is a national stage filing under 35 U.S.C. § 371 of international application PCT/EP2010/058064, filed Jun. 9, 2010, which was published under PCT Article 21(2) in English, the disclosure of which is incorporated by reference herein in its entirety.

FIELD OF THE INVENTION

The present invention relates to the field of cardiovascular diseases or disorders. More specifically, it relates to markers and methods for determining whether a subject, particularly a human subject, is at risk of developing cardiovascular disease, having cardiovascular disease, or experiencing a complication of a cardiovascular disease. The present invention also relates to the use of such markers and methods for monitoring the status of cardiovascular risk and/or disease in a subject or the effects of preventive and/or therapeutic measures/agents on subjects with cardiovascular risk or cardiovascular disease.

TECHNICAL BACKGROUND

Cardiovascular disease (CVD) is a term for heart and blood vessel diseases, including—among others—ischemic heart disease (being the most common type of CVD in the industrialized countries; this disorder refers to problems with the circulation of the blood to the heart muscle), cerebrovascular disease (refers to a problem with the circulation of the blood in the blood vessels of the brain), and peripheral vascular disease (affecting the circulation primarily in the legs). Subjects with CVD may develop a number of complications (hereinafter referred to as CVD complications) including, but not limited to, myocardial infarction, stroke, angina pectoris, transient ischemic attacks, congestive heart failure, aortic aneurysm and death.

The *Framingham Heart Study* (Kamel W B et al. Am J Cardiol 1988; 62:1109-1112., Wilson P W F et al., Circulation 1988; 97:1837-1847, Grundy S. M. et al. Circulation 1988; 97:1876-1887) was a pioneering study in the development of the concept of risk factors, which is widely used and accepted today. Several independent risk factors have been recognized to be the direct cause of coronary disease and are frequent factors in the population, and their modification reduces the risk of coronary (i.e. cardiovascular) events (Grundy S. C. et al., Circulation 2000; 101:e3-e11). The main modifiable risk factors are smoking, high blood pressure, hypercholesterolemia (in particular high LDL-cholesterol) and diabetes mellitus (Circulation 2000; 101: e3-e11).

The adaptation of all actions according to the absolute risk (the probability that a person develops a coronary disease in a certain period of time) is important, because it allows to reach a suitable balance between efficacy, safety and therapy costs. The estimation of the absolute risk requires adding up the contribution of each risk factor and the result is "the determination of the global risk". The *Framingham Heart Study*, as mentioned above, performed a quantitative estimation of the global risk based on the contribution of each risk factor that has served other Societies to develop other algorithms for other populations. The incidence and emergence of cardiovascular disease in Europe differs significantly from the USA, and the Framingham scale has been reported to overestimate cardiovascular risk in the European population (Moreno J et al., Rev Med Univ Navarra 2005; 49:109-115).

For this reason, two scales have been developed to estimate cardiovascular risk in Europe: the PROCAM scale that estimates the risk of cardiovascular complications (Assman G et al., Circulation 2002; 105:310-315) and the SCORE Project (Conroy R. M. et al., Eur Heart J 2003; 24:987-1003), which estimates the risk of cardiovascular death.

However, in spite of all efforts made to estimate risk and despite the recommendation to estimate the global cardiovascular risk in all patients, a considerable number of cardiovascular events occur in asymptomatic patients with an intermediate risk according to the risk assessment tools (Circulation 2001; 104:1863-1867).

Patients with an intermediate risk would significantly benefit from the use of more tests that allowed a more precise stratification of their risk (Circulation 2001; 104: 1863-1867, Am J Cardiol 2006; 97 [Suppl]:28A-32A).

Several studies have identified genetic markers which associate with the risk of suffering a CVD.

In particular, three studies which are analyzing if the incorporation of genetic information in the classic functions of risk improves their predictive and discriminatory capabilities have been published. The first one published by Morrison et al., (Am J Epidemiol. 2007 Jul. 1; 166(1):28-35) with a follow-up of more than 15.000 participants of the study ARIC, constructed in this cohort a scale of genetic risk including 11 polymorphisms. However, this function does not improve the capacity of discrimination of the classic risk factors (the area under the curve ROC was increasing only slightly from 0.764 to 0.766).

The second one, published by Kathiresan et al. (N Engl J Med. 2008 Mar. 20; 358(12):1240-9) also used a function of genetic risk including 9 polymorphisms related to lipid metabolism, also based on the number of alleles of risk in each subject. This function of genetic risk was independently related to the appearance of cardiovascular events in the cohort of Malmo. Though this punctuation was not improving the capacity of discrimination of the classic risk factors (area under the curve ROC, 0,8 with and without the genetic information), the reclassification was improved.

The third and most recent paper was a study performed in a cohort of American nurses. The incorporation of the genetic variability in the chromosome 9p21.3 does not improve the capacity of discrimination (area under the curve ROC from 0,807 to 0,809) nor the reclassification of individuals with regard to that obtained with the classical risk factors (Ann Intern Med. 2009 Jan. 20; 150(2):65-72).

Therefore, despite several attempts made to improve the prediction power of the CVRF this goal has not yet been accomplished.

Accordingly, there is a need for novel markers, including new genetic markers and combinations thereof that could successfully and advantageously predict who is at higher risk of developing classical cardiovascular risk factors in a way that preventive measures could be implemented to keep the cardiovascular risk at the lower possible level.

SUMMARY OF THE INVENTION

In a first aspect, the invention provides a method of determining whether a subject has an increased risk of having an adverse cardiovascular disease or disorder or of determining the response to a cardiovascular therapy in a subject comprising the steps of determining in a sample isolated from said subject the presence of polymorphisms at positions 27 within the nucleic acid sequences of SEQ ID NO:1 to 11, wherein the presence at position 27 of a C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and T in SEQ ID NO:11 is indicative of an increased risk of having an adverse cardiovascular disease or disorder or of a low response to a cardiovascular therapy.

The invention further provides a method for identifying a subject in need of early and/or aggressive cardiovascular therapy or in need of prophylactic cardiovascular therapy comprising the steps of determining in a sample isolated from said subject the presence in at least one allele of polymorphisms at positions 27 within a nucleic acid sequences of SEQ ID NO:1 to 11, wherein the presence at position 27 of a C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and T in SEQ ID NO:11 is indicative of having a decreased response to a cardiovascular therapy or of being in need of early and aggressive cardiovascular therapy or in need of prophylactic cardiovascular treatment.

In another aspect, the invention relates to a method of treatment of a patient suffering from a cardiovascular disease with a cardiovascular therapy wherein the patient is selected for said therapy based on the presence in a sample isolated from said subject of a polymorphism at position 27 in the nucleotide sequences of SEQ ID NO:1 to 11, wherein said polymorphism at said position 27 is C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and T in SEQ ID NO:11.

In further aspects, the invention relates to methods for the determination of the probability of an individual of presenting a fatal or non-fatal myocardial infarction or angina in a 10 year period based on the presence of one or more of the polymorphisms mentioned above in combination with one or more conventional risk factors, wherein the relative contribution of each polymorphism or risk factor to the probability is corrected using the hazard ratios.

In a further aspect, the invention relates to a computer program or a computer-readable media containing means for carrying out any of the methods of the invention.

In yet a further aspect, the invention relates to a kit comprising reagents for detecting the identity of the nucleotide at position 27 within a nucleic acid sequence selected from the group of SEQ ID NO:1 to 11.

DETAILED DESCRIPTION OF THE INVENTION

The authors of the present invention have identified a series of single nucleotide polymorphism (SNP) markers which, when used in combination, are associated with a risk of CVD and/or with a risk of CVD complications including, but not limited to, myocardial infarction, stroke, angina pectoris, transient ischemic attacks, congestive heart failure, aortic aneurysm and death. These polymorphic markers appear to show predictive value independently of classical risk factors such as high LDL and VLDL levels, smoking habits, low levels of HDL, high levels of lipoprotein A, hypertension, diabetes, high homocysteine levels, high levels of hemostatic factors, metabolic syndrome, insulin resistance, familiar story and the like and are superior to the polymorphisms used individually or to conventional cardiovascular risk factors.

Method for Determining Whether a Subject has an Altered Risk of Having an Adverse Cardiovascular Disease In a first aspect, the invention relates to a method (hereinafter the first method of the invention) of determining whether a subject has an altered risk of having an adverse cardiovascular disease or disorder or of determining the response to a cardiovascular therapy in a subject comprising the steps of determining in a sample isolated from said subject the identity of the nucleotide at position 27 within a nucleic acid sequence selected from the group of SEQ ID NO:1 to 11 (see table 1), wherein the presence at position 27 of a C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and/or T in SEQ ID NO:11 is indicative of an increased risk of having an adverse cardiovascular disease or disorder or of a low response to a cardiovascular therapy.

The terms "polymorphism" and "single nucleotide polymorphism" (SNP) are used herein interchangeably and relate to a nucleotide sequence variation occurring when a single nucleotide in the genome or another shared sequence differs between members of species or between paired chromosomes in an individual. A SNP can also be designated as a mutation with low allele frequency greater than about 1% in a defined population. Single nucleotide polymorphisms according to the present application may fall within coding sequences of genes, non-coding regions of genes or the intronic regions between genes.

The list of polymorphisms which are used in the method of the present invention is given in Table 1.

TABLE 1

Polymorphisms used in the method of the invention including SEQ ID NO:, the sequences flanking the polymorphism and the polymorphic position (underlined), the accession number in dbSNP, the chromosome and position in the chromosome where the polymorph is found and the accession number and database build of the sequence of the chromosomal fragment.

| SEQ ID NO: | Sequence comprising the polymorphism | dbSNP accession number | Allele of risk | Chrom. | Position in chrom. | Strand | Accession number/ Build |
|---|---|---|---|---|---|---|---|
| 1 | TCATACTAACCATATGATCAACAGTTCAAAAGCAGC CACTCGCAGAGGTAAG | rs1333049 | C | 9 | 22063860 | + | AC_000052/ 03.03.2008 |
| 2 | AAAGAGAAAGAAATAGGAGCAGGATCAACTTCCAGA TATACAGAGAATATAA | rs599839 | A | 1 | 109623689 | + | NC_000001/ 03.03.2008 |

TABLE 1-continued

Polymorphisms used in the method of the invention including SEQ ID NO:, the sequences flanking the polymorphism and the polymorphic position (underlined), the accession number in dbSNP, the chromosome and position in the chromosome where the polymorph is found and the accession number and database build of the sequence of the chromosomal fragment.

| SEQ ID NO: | Sequence comprising the polymorphism | dbSNP accession number | Allele of risk | Chrom. | Position in chrom. | Strand | Accession number/ Build |
|---|---|---|---|---|---|---|---|
| 3 | AACCATAATAAGTTATGCTGAGAAGTTCTTTTTTGTCATAGTGCAAGATAACA | rs17465637 | C | 1 | 196042601 | + | AC_000044/ 03.03.2008 |
| 4 | TTGAAAAAATTAATTCTCACACTCCTAAGTGCATTTAATTTAAGCTACTTT | rs501120 | T | 10 | 40757334 | + | AC_000053/ 03.03.2008 |
| 5 | AAAAGCAAGCACATGTGTGGCATTACCAACATTAAATATTTATATACATAGT | rs2943634 | C | 2 | 220837297 | + | AC_000045/ 03.03.2008 |
| 6 | ACAGTTTTTACTGTAACTGCCAATAAATAATACTCATCTTTAAAAAGACATC | rs6922269 | A | 6 | 151294678 | + | NC_000006/ 03.03.2008 |
| 7 | GGCAAGTACCTGGGCACAGGGCTGCTTCATGGCCTTGGACCTGGACAGTGGA | rs9982601 | T | 21 | 20798690 | + | AC_000064/ 03.03.2008 |
| 8 | ACATCTGCCTCTCTAGACTATAAACTCTTTGGGGCTAGGTCTTCTTTGTCTT | rs12526453 | C | 6 | 14155621 | + | AC_000049/ 03.03.2008 |
| 9 | GCTATCATTTAAATTTGGTTGAGACACAATATGCTGTTGCACTTTCTATAAA | rs6725887 | C | 2 | 197498571 | + | AC_000045/ 03.03.2008 |
| 10 | CTGTGCTGCTTGGTGCCTCTCTGATATGAATACACTGACACGTCAAAGTAAC | rs9818870 | T | 3 | 136547031 | + | AC_000046/ 03.03.2008 |
| 11 | CTTGCTCCAGCATCCAGGAGGTCCGGTGGTGCACACGGCTTGAGATGCCTGA | rs3184504 | T | 12 | 111511042 | + | AC_000055/ 03.03.2008 |

The following embodiment of Table 1A is particularly preferred.

TABLE 1A

| Patent SEQ ID NO: | Variante | Allele of risk | Chrom | Gen | Position in chrom | Strand | Accession number/ Build | Sequence comprising the polymorphism |
|---|---|---|---|---|---|---|---|---|
| 1 | rs1333049 | C | 9 | CDKN2A/2B | 22063860 | + | AC_000052/ 0.03.2008 | 1. TCATACTAACCATATGATCAACAGTTCAAAAGCAGCCACTCGCAGAGCTAAG |
| 3 | rs17465637 | C | 1 | MIA3 | 196042601 | + | AC_000044/ 03.03.2008 | 3. AACCATAATAAGTTATGCTGAGAAGTTCTTTTTTGTCATAGTGCAAGATAACA |
| 4 | rs501120 | T | 10 | CXCL12 | 40757334 | + | AC_000053/ 03.03.2008 | |
| 6 | rs6922269 | A | 6 | MTHFD1L | 151294678 | + | NC_000006/ 03.03.2008 | 6. ACAGTTTTTACTGTAACTGCCAATAAATAATACTCATCTTTAAAAAGACATC |
| 7 | rs9982601 | T | 21 | SLC5A3, MRPS6 | 20798690 | + | AC_000064/ 03.03.2008 | 7. GGCAAGTACCTGGGCACAGGGCTGCTTCATGGCCTTGGACCTGGACAGTGGA |
| 8 | rs12526453 | C | 6 | PHACTR1 | 14155621 | + | AC_000049/ 03.03.2008 | 8. ACATCTGCCTCTCTAGACTATAAACTCTTTGGGGCTAGGTCTTCTTTGTCTT |
| 9 | rs6725887 | C | 2 | | 197498571 | + | AC_000045/ 03.03.2008 | 9. GCTATCATTTAAATTTGGTTGAGACACAATATGCTGTTGCACTTTCTATAAA |
| 10 | rs9818870 | T | 3 | MRAS | 136547031 | + | AC_000046/ 003.03.208 | 10. CTGTGCTGCTTGGTGCCTCTCTGATATGAATACACTGACACGTCAAAGTAAC |

TABLE 1A-continued

| Patent SEQ ID NO: | Variante | Allele of risk | Chrom | Gen | Position in chrom | Strand | Accession number/ Build | Sequence comprising the polymorphism |
|---|---|---|---|---|---|---|---|---|
| 12 | rs17228212 | C | 15 | SMAD3 | | | | 12. AGATCACACTGTCTTTGCCGTCATTGA ACTCGCAACCTAACTGCTGAGTGAGGA CACGTCC (SEQ ID NO: 12) |

As for variant 4 above, this could also be analyzed by searching for rs1746048 which is in linkage disequilibrium thereto (allele of risk: T), "variant 4a".
As for variant 6 above, this could also be analyzed by looking for rs1474787 that is in linkage disequilibrium thereto (allele of risk: G), "variant 6a".
As for variant 7 above, this could also be analyzed by looking for rs9978407 that is in linkage disequilibrium thereto (allele of risk: G), "variant 7a".
Sequence comprising the polymorphisms:
Variant 4a: GAAGGGTAAAGGGTGGTAGGATTGAGTGAGTCAGGCCAGAAACCTCTAGTTA (SEQ ID NO: 13)
Variant 6a: AGGACAATGCTCACCCTCTTTGCACCGCTATCACATCACCTGTTCAGGGCAC (SEQ ID NO: 14)
Variant 7a: TACAGGATTCAACAATTAGTCAAAAAGTCATGAGCTAACAAAATAGGAGCTT (SEQ ID NO: 15)

The term "determining whether a subject has an altered risk", as used herein, relates to the assessment of the probability according to which a subject is going to suffer from a disease. The term "determining the response to a cardiovascular therapy", as used herein, relates to the assessment of the probability with which a subject is going to respond to a therapy. As will be understood by those skilled in the art, such an assessment, although preferred to be, may usually not be correct for 100% of the subjects to be diagnosed or evaluated. The term, however, requires that a statistically significant portion of subjects can be identified as having an increased risk or as being responsive to the therapy. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably, 0.2, 0.1 or 0.05.

The term "cardiovascular disease or disorder", as used herein, includes diseases affecting the heart or blood vessels or both or associated with the cardiopulmonary and circulatory systems including but not limited to ischemia, angina, edematous conditions, artherosclerosis, Coronary Heart Disease, LDL oxidation, adhesion of monocytes to endothelial cells, foam-cell formation, fatty-streak development, platelet adherence, and aggregation, smooth muscle cell proliferation, reperfusion injury, high blood pressure, thrombotic disease, arrhythmia (atrial or ventricular or both); cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue, endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In a preferred embodiment, the cardiovascular disease which risk is to be detected is selected from the group of myocardial infarction, stroke, angina pectoris, transient ischemic attacks, congestive heart failure, aortic aneurysm or a combination thereof.

The term "cardiovascular therapy", as used herein, refers to any type of treatment which results in the amelioration or reduces the risk of suffering any of the above mentioned cardiovascular diseases. Suitable therapies for use in the present invention include, without limitation, anticoagulants, antiplatelet agents, thrombolytic agents, antithrombotics, antiarrhythmic agents, agents that prolong repolarization, antihypertensive agents, vasodilator, antihypertensives, diuretics, inotropic agents, antianginal agents and the like.

Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Non-limiting examples of antiplatelet agents include aspirin, a dextran, dipyridamole (persantin), heparin, sulfinpyranone (anturane), clopidrogel and ticlopidine (ticlid). No limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a patient is suffering from a hemorrhage or an increased likelihood of hemorrhaging, an agent that may enhance blood coagulation may be used. Non-limiting examples of a blood coagulation promoting agents include thrombolytic agent antagonists and anticoagulant antagonists. Non-limiting examples of anticoagulant antagonists include protamine and vitamine KI.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

Non-limiting examples of antiarrhythmic agents include Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythmic agents.

Non-limiting examples of sodium channel blockers include Class IA, Class IB and Class IC antiarrhythmic agents. Non-limiting examples of Class IA antiarrhythmic agents include dispyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

Non-limiting examples of beta blockers, otherwise known as beta-adrenergic blocker, a beta-adrenergic antagonists or Class II antiarrhythmic agents, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain embodiments, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Non-limiting examples of agents with hypolipemic capabilities include, without limitation, bile acid sequestrants such as quatemary amines (e.g. cholestyramine and colestipol); nicotinic acid and its derivatives; HMG-CoA reductase inhibitors such as mevastatin, pravastatin, and simvastatin; gemfibrozil and other fabric acids, such as clofibrate, fenofibrate, benzafibrate and cipofibrate; probucol; raloxifene and its derivatives.

Non-limiting examples of agents that prolong repolarization, also known as Class III antiarrhythmic agents, include amiodarone (cordarone) and sotalol (betapace).

Non-limiting examples of calcium channel blocker, otherwise known as Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinide derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

Non-limiting examples of miscellaneous antiarrhythmic agents include adenosine (adenocard), digoxin (lanoxin), acecainide, ajmaline, amoproxan, aprindine, bretylium tosylate, bunaftine, butobendine, capobenic acid, cifenline, disopyranide, hydro quinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of alpha blocker, also known as alpha-adrenergic blocker or an alpha-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an a blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an a and beta adrenergic antagonist. Non-limiting examples of an alpha/beta blocker comprise labetalol (normodyne, trandate).

Non-limiting examples of anti-angiotensin II agents include angiotensin converting enzyme inhibitors and angiotensin II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of angiotensin II receptor blocker, also known as angiotensin II receptor antagonist, ANG receptor blockers or an ANG-II type-1 receptor blockers (ARBS), include angiocandesartan, eprosartan, irbesartan, losartan and valsartan. Non-limiting examples of sympatholytics include centrally acting sympatholytics or peripherially acting sympatholytic. Non-limiting examples of centrally acting sympatholytics, also known as central nervous system (CNS) sympatholytics, include clonidine (catapres), guanabenz (wytensin) guanfacine (tenex) and methyldopa (aldomet). Non-limiting examples of a peripherally acting sympatholytic include ganglion blocking agents, an adrenergic neuron blocking agent, a beta-adrenergic blocking agent or an alpha-adrenergic blocking agent. Non-limiting examples of ganglion blocking agents include mecamylamine (inversine) and trimethaphan (arfonad). Non-limiting examples of adrenergic neuron blocking agents include guanethidine (ismelin) and reserpine (serpasil). Non-limiting examples of beta-adrenergic blockers include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha-adrenergic blockers include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of coronary vasodilators include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(beta-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricromyl, trimetazidine, trolnitrate phosphate and visnadine.

In certain embodiments, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, gamma-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive may comprise an arylethanolamine derivative, a benzothiadiazine derivative, a 7V-carboxyalkyl(peptide/lactam) derivative, a dihydropyridine derivative, a guanidine derivative, a hydrazines/phthalazine, an imidazole derivative, a quantemary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril. Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todralazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide. Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine. Non-limiting examples of agents for the treatment of congestive heart failure include anti-angiotensin II agents, afterload-preload reduction treatment, diuretics and inotropic agents.

In certain embodiments, an animal, e.g. a human, patient that cannot tolerate an angiotensin antagonist may be treated with a combination therapy. Such therapy may combine adminstration of hydralazine (apresoline) and isosorbide dinitrate (isordil, sorbitrate).

Non-limiting examples of diuretics include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

Non-limiting examples of positive inotropic agents, also known as cardiotonics, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular embodiments, an intropic agent is a cardiac glycoside, beta-adrenergic agonist or a phosphodiesterase inhibitor. Non-limiting examples of cardiac glycosides include digoxin (lanoxin) and digitoxin (crystodigin). Non-limiting examples of beta-adrenergic agonists include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethy norepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole). Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor. Inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

The term "sample", as used herein, refers to any sample from a biological source and includes, without limitation, cell cultures or extracts thereof, biopsied material obtained from a mammal or extracts thereof, and blood, saliva, urine, feces, semen, tears, or other body fluids or extracts thereof.

Those skilled in the art will readily recognize that the analysis of the nucleotides present according to the method of the invention in an individual's nucleic acid can be done by any method or technique capable of determining nucleotides present in a polymorphic site. As it is obvious in the art the nucleotides present in the polymorphic markers can be determined from either nucleic acid strand or from both strands.

Once a biologic sample from a subject has been obtained (e.g., a bodily fluid, such as urine, saliva, plasma, serum, or a tissue sample, such as buccal tissue sample or buccal cell) detection of a sequence variation or allelic variant SNP is typically undertaken. Virtually any method known to the skilled artisan is employed. Perhaps the most direct method is to actually determine the sequence of either genomic DNA or cDNA and compare these sequences to the known alleles SNPs of the gene. This can be a fairly expensive and time-consuming process. Nevertheless, this technology is quite commonly and is well known.

Any of a variety of methods that exist for detecting sequence variations may be used in the methods of the invention. The particular method used is not important in the estimation of cardiovascular risk or treatment selection.

Another possible commercially available methods exist for the high throughput SNP identification not using direct sequencing technologies. For example, Illumina's Veracode Technology, Taqman® SNP Genotyping Chemistry and KASPar SNP genotyping Chemistry.

A variation on the direct sequence determination method is the Gene Chip™ method available from Affymetrix. Alternatively, robust and less expensive ways of detecting DNA sequence variation are also commercially available. For example, Perkin Elmer adapted its TAQman Assay™ to detect sequence variation. Orchid BioSciences has a method called SNP-IT™. (SNP-Identification Technology) that uses primer extension with labeled nucleotide analogs to determine which nucleotide occurs at the position immediately 3' of an oligonucleotide probe, the extended base is then identified using direct fluorescence, indirect colorimetric assay, mass spectrometry, or fluorescence polarization. Sequenom uses a hybridization capture technology plus MALDI-TOF (Matrix Assisted Laser Desorption/Ionization—Time-of-Flight mass spectrometry) to detect SNP genotypes with their MassARRAY™ system. Promega provides the READIT™ SNP/Genotyping System (U.S. Pat. No. 6,159,693). In this method, DNA or RNA probes are hybridized to target nucleic acid sequences. Probes that are complementary to the target sequence at each base are depolymerized with a proprietary mixture of enzymes, while probes which differ from the target at the interrogation position remain intact. The method uses pyrophosphorylation chemistry in combination with luciferase detection to provide a highly sensitive and adaptable SNP scoring system. Third Wave Technologies has the Invader OS™ method that uses a proprietary Cleavaseg enzymes, which recognize and cut only the specific structure formed during the Invader process. Invader OS relies on linear amplification of the signal generated by the Invader process, rather than on exponential amplification of the target. The Invader OS assay does not utilize PCR in any part of the assay. In addition, there are a number of forensic DNA testing labs and many research labs that use gene-specific PCR, followed by restriction endonuclease digestion and gel electrophoresis (or other size separation technology) to detect restriction fragment length polymorphisms (RFLPs).

In various embodiments of any of the above aspects, the presence or absence of the SNPs is identified by amplifying or failing to amplify an amplification product from the sample. Polynucleotide amplifications are typically template-dependent. Such amplifications generally rely on the existence of a template strand to make additional copies of the template. Primers are short nucleic acids that are capable of priming the synthesis of a nascent nucleic acid in a template-dependent process, which hybridize to the template strand. Typically, primers are from ten to thirty base pairs in length, but longer sequences can be employed. Primers may be provided in double-stranded and/or single-stranded form, although the single-stranded form generally is preferred. Often, pairs of primers are designed to selectively hybridize to distinct regions of a template nucleic acid, and are contacted with the template DNA under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

Polymerase Chain Reaction

A number of template dependent processes are available to amplify the oligonucleotide sequences present in a given template sample. One of the best known amplification methods is the polymerase chain reaction. In PCR, pairs of primers that selectively hybridize to nucleic acids are used under conditions that permit selective hybridization. The term primer, as used herein, encompasses any nucleic acid that is capable of priming the synthesis of a nascent nucleic acid in a template-dependent process. Primers may be provided in double-stranded or single-stranded form, although the single-stranded form is preferred. Primers are used in any one of a number of template dependent processes to amplify the target gene sequences present in a given template sample. One of the best known amplification methods is PCR, which is described in detail in U.S. Pat. Nos. 4,683,195, 4,683,202 and 4,800,159, each incorporated herein by reference. In PCR, two primer sequences are prepared which are complementary to regions on opposite complementary strands of the target-gene(s) sequence. The primers will hybridize to form a nucleic-acid:primer complex if the target-gene(s) sequence is present in a sample. An excess of deoxyribonucleoside triphosphates is added to a reaction mixture along with a DNA polymerase, e.g., Taq polymerase, that facilitates template-dependent nucleic acid synthesis. If the target-gene(s) sequence:primer complex has been formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles", are conducted until a sufficient amount of amplification product is produced.

The amplification product may be digested with a restriction enzyme before analysis. In still other embodiments of any of the above aspects, the presence or absence of the SNP is identified by hybridizing the nucleic acid sample with a primer labeled with a detectable moiety. In other embodiments of any of the above aspects, the detectable moiety is detected in an enzymatic assay, radioassay, immunoassay, or by detecting fluorescence. In other embodiments of any of the above aspects, the primer is labeled with a detectable dye (e.g., SYBR Green I, YO-PRO-I, thiazole orange, Hex, pico green, edans, fluorescein, FAM, or TET). In other embodiments of any of the above aspects, the primers are located on a chip. In other embodiments of any of the above aspects, the primers for amplification are specific for said SNPs.

Another method for amplification is the ligase chain reaction ("LCR"). LCR differs from PCR because it amplifies the probe molecule rather than producing amplicon through polymerization of nucleotides. In LCR, two complementary probe pairs are prepared, and in the presence of a target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

Isothermal Amplification

An isothermal amplification method, in which restriction endonucleases and ligases are used to achieve the amplification of target molecules that contain nucleotide 5'-[[alpha]-thio]-triphosphates in one strand of a restriction site also may be useful in the amplification of nucleic acids in the present invention. In one embodiment, loop-mediated isothermal amplification (LAMP) method is used for single nucleotide polymorphism (SNP) typing.

Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection.

Transcription-Based Amplification

Other nucleic acid amplification procedures include transcription-based amplification systems, including nucleic acid sequence based amplification. In nucleic acid sequence based amplification, the nucleic acids are prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer, which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Other amplification methods may be used in accordance with the present invention. In one embodiment, "modified" primers are used in a PCR-like, template and enzyme dependent synthesis. The primers may be modified by labeling with a capture moiety (e.g., biotin) and/or a detector moiety (e.g., enzyme). In the presence of a target sequence, the probe binds and is cleaved catalytically. After cleavage, the target sequence is released intact to be bound by excess probe. Cleavage of the labeled probe signals the presence of the target sequence. In another approach, a nucleic acid amplification process involves cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Methods for Nucleic Acid Separation

It may be desirable to separate nucleic acid products from other materials, such as template and excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid. Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC. In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized with light exhibiting the appropriate excitatory spectra.

Alternatively, the presence of the polymorphic positions according to the method of the invention can be determined by hybridisation or lack of hybridisation with a suitable nucleic acid probe specific for a polymorphic nucleic acid but not with the non-mutated nucleic acid. By "hybridize" is meant pair to form a double-stranded molecule between complementary polynucleotide sequences, or portions thereof, under various conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 [mu]g/ml denatured salmon sperm DNA (ssDNA). In a most preferred embodiment, hybridization will occur at 42° C. in 250 mM NaCl, 25 mM trisodium citrate, 1% SDS, 50% formamide, and 200 [mu]g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Nucleic acid molecules useful for hybridisation in the methods of the invention include any nucleic acid molecule which exhibits substantial identity so as to be able to specifically hybridise with the target nucleic acids. Polynucleotides having "substantial identity" to an endogenous sequence are typically capable of hybridizing with at least one strand of a double-stranded nucleic acid molecule. By "substantially identical" is meant a polypeptide or nucleic acid molecule exhibiting at least 50% identity to a reference amino acid sequence or nucleic acid sequence. Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e<"3> and e<"100> indicating a closely related sequence.

A detection system may be used to measure the absence, presence, and amount of hybridization for all of the distinct sequences simultaneously. Preferably, a scanner is used to determine the levels and patterns of fluorescence.

The expression "increased risk of having an adverse cardiovascular disease or disorder" is understood as showing a propensity of suffering such a disease higher than the average in the population.

The expression "low response to a cardiovascular therapy" is meant having an reduced reaction to therapy. Where a subject has a reduced responsiveness to therapy, an increased amount or number of therapeutic agents is required to achieve a given therapeutic effect. Suitable cardiovascular therapies to be applied to subjects selected according to the method of the present invention have been described in detail above.

Method for Identifying a Subject in Need of Early and/or Aggressive Cardiovascular Therapy or in Need of Prophylactic Cardiovascular Therapy In another aspect, the invention relates to a method (hereinafter the second method of the invention) for identifying a subject in need of early and/or aggressive cardiovascular therapy or in need of prophylactic cardiovascular therapy comprising the steps of determining in a sample isolated from said subject the identity of the nucleotide at position 27 within a nucleic acid sequence selected from the group of SEQ ID NO:1 to 11, wherein the presence at position 27 of a C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and/or T in SEQ ID NO:11 is indicative of having a decreased response to a cardiovascular therapy or of being in need of early and aggressive cardiovascular therapy or in need of prophylactic cardiovascular therapy.

The term "cardiovascular therapy" has been defined in detail in the first method of the invention.

By "early and aggressive cardiovascular therapy" is meant a treatment approach that aims to control blood pressure rapidly, which for some individuals will require the use of multiple antihypertensive drugs. If desirable, such therapy may also include glucose control, lipid metabolism control, weight loss control, and smoking cessation.

As described above, the specific methods or compositions used to detect polymorphisms (e.g., SNPS, RFLPs) are not significant. The invention employs virtually any method for detecting an allele variation that is known in the art.

The key in risk determination and treatment selection is the identification of particular allelic SNP and the correlation of these sequence SNPs with treatment selection, therapy benefit, or risk of an adverse cardiovascular event. This genetic information is useful in isolation, but may be even more useful when coupled with other factors of clinical significance to cardiovascular health. Such factors include age, race, sex, body mass index, blood pressure, smoking status, alcohol consumption history, smoking history, exercise history, diet, family history of cardiovascular disease, low density lipoprotein (LDL)- or high density lipoprotein (HDL)-cholesterol (HDL) level, systolic blood pressure, diastolic blood pressure, history of heart failure, diabetes, renal insufficiency, or left ventricular hypertrophy. Thus, in another aspect, the first and second method of the invention may further include the determination of classical risk factors.

Suitable classical risk factors for use in the methods of the present invention include, without limitation, age, race, sex, body mass index, blood pressure, smoking status, alcohol consumption history, smoking history, exercise history, diet, family history of cardiovascular disease, low density lipoprotein (LDL)- or high density lipoprotein (HDL)-cholesterol level, systolic blood pressure, diastolic blood pressure, history of heart failure, diabetes, renal insufficiency, or left ventricular hypertrophy.

Preferred sets of classical risk markers include those forming part of known models for predicting the risk of CVD such as the Framingham original and also those derived from it such as but not limited to REGICOR, and SCORE, PROCAM or QRISK models. Classical risk factors used in the Framingham model and in those derived from it include age, total cholesterol, HDL-cholesterol, blood pressure, diabetes and smoking status. Classical risk factors used in the REGICOR model include age, sex, cholesterol, HDL-cholesterol, systolic arterial pressure, diabetic status and smoking status. Classical risk factors used in the SCORE model include age, cholesterol, systolic arterial pressure and smoking status. Classical risk factors used in the PROCAM model include age, sex, LDL-cholesterol, HDL-cholesterol, triglycerides, arterial systolic pressure, diabetic status, smoking status, family history of myocardial infarction. Classical risk factors used in the QRISK model include age, total cholesterol/HDL cholesterol ratio, body mass index, family history of premature CVD, smoker status, Townsend score of output area, systolic blood pressure, treatment for hypertension and interaction SBP*HTN treatment.

The invention can employ metrics (e.g., mathematical methods) for evaluating whether a relationship exists between genetic information and risk of an adverse cardiovascular outcome. The predictive accuracy of such methods is generally improved when the effect of one or more other factors on cardiovascular prognosis is considered. A metric mathematical method may be used, for example, to correlate a cardiovascular disease or the propensity probability to develop a cardiovascular disease or disorder with a (variant) allele SNP of a nucleic acid molecule of interest, alone or in combination with other factors. In one embodiment, a metric (e.g., an algorithm or mathematical formula) is used to determine whether a correlation exists between the presence of an allele variant SNP and a cardiovascular disease or adverse cardiovascular event.

Personalised Medicine Methods of the Invention

The SNP signature identified by the authors of the present invention is also suitable for selecting patients to apply a cardiovascular treatment to a patient wherein said patient has been previously selected on the basis of the presence of a risk factor for CVD calculated from said SNP signature. Thus, it is an object of the present invention to provide a method of treatment of a patient suffering from a cardiovascular disease with a cardiovascular therapy wherein the patient is selected for said therapy based on the presence in a sample isolated from said subject of a polymorphism at position 27 in the nucleotide sequences of SEQ ID NO:1 to 11, wherein said polymorphism at said position 27 is C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and T in SEQ ID NO:11.

It is another object of the present invention to provide the use of a cardiovascular therapy for the preparation of a medicament for the treatment of a patient suffering from a cardiovascular disease with a wherein the patient is selected for said therapy based on the presence in a sample isolated from said subject of a polymorphism at position 27 in the nucleotide sequences of SEQ ID NO:1 to 11, wherein said polymorphism at said position 27 is C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and T in SEQ ID NO:11.

It is another object of the present invention to provide a cardiovascular therapy for use in the treatment of a patient from a cardiovascular disease wherein the patient is selected for said therapy based on the presence in a sample isolated from said subject of a polymorphism at position 27 in the nucleotide sequences of SEQ ID NO:1 to 11, wherein said polymorphism at said position 27 is C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and T in SEQ ID NO:11

The expressions "cardiovascular therapy" and "cardiovascular disease" have been explained in detailed previously. In a preferred embodiment, the cardiovascular therapy is a beta blocker therapy or verapamil therapy. In yet another embodiment, the cardiovascular disease is selected from the group of myocardial infarction, stroke, angina pectoris, transient ischemic attacks, congestive heart failure, aortic aneurysm or a combination thereof.

The agents forming the cardiovascular therapy may be administered to humans and other animals by any suitable route of administration, including orally, nasally, as by, for example, a spray, rectally, intravaginally, parenterally, intracisternally and topically, as by powders, ointments or drops, including buccally and sublingually. Actual dosage levels of the one or more agents administered in the methods of the present invention may be varied so as to obtain an amount of the active ingredient which is effective to achieve a response in an animal. The actual effective amount can be determined by one of skill in the art using routine experimentation and may vary by mode of administration. Further, the effective amount may vary according to a variety of factors include the size, age and gender of the individual being treated. Additionally, the severity of the condition being treated, as well as the presence or absence of other components to the individual treatment regimen will influence the actual dosage. The effective amount or dosage level will depend upon a variety of factors including the activity of the particular one or more agents employed, the route of administration, the time of administration, the rate of excretion of the particular agents being employed, the duration of the treatment, other drugs, compounds and/or materials used in combination with the particular agents employed, the age, sex, weight, condition, general health and prior medical history of the animal, and like factors well known in the medical arts.

The personalized medicine method of the invention may also include the determination of classical risk factors such as age, race, sex, body mass index, blood pressure, smoking status, low density lipoprotein (LDL)- or high density lipoprotein (HDL)-cholesterol level, systolic blood pressure, diastolic blood pressure, history of heart failure, diabetes, renal insufficiency, or left ventricular hypertrophy, alcohol consumption history, smoking history, exercise history, diet, and family history of cardiovascular disease; and correlating the presence of the SNP and one or more cardiovascular disease risk factors with the need for a personalized, possibly early and aggressive cardiovascular therapy, where a positive correlation identifies the subject as having an altered, in particular increased, risk for an adverse cardiovascular disease or disorder. In one embodiment, the method further involves selecting an appropriate treatment regimen. In another embodiment, the method further involves administering the treatment regimen to the subject.

Methods for Determining the Cardiovascular Risk in a Subject

Another object of the present invention is the improvement of the CVRFs nowadays in use by introducing in the function the risk conferred by the particular combination of SNP markers as set out in table 1 associated with a risk of CVD and/or with a risk of CVD complications including, but not limited to, myocardial infarction, stroke, angina pectoris, transient ischemic attacks, congestive heart failure, aortic aneurysm and death. CVRFs nowadays in use include, but are not limited to, the original Framingham function, the adapted Framingham function (such as but not limited to REGICOR function), PROCAM function, SCORE function, and QRISK function. The improvement of the Framingham, PROCAM, REGICOR and QRISK functions is shown as functions 1a and 1b.

Function 1a

This general equation can be used to calculate the coronary or cardiovascular risk using the risk factors and effects of the risk factors included and defined in the Framingham (the original and/or the adapted such as but not limited to REGICOR), PROCAM and QRISK functions:

wherein, $$prob(event_i \mid CRF_{p,i}, SNP_{j,i}) = 1 - \hat{S}^{\exp\left[\sum_{p=1}^{P} \beta_{CRF_p} * CRF_{p,i} + \sum_{j=1}^{J} \beta_{SNP_j} * SNP_{j,i} - \sum_{p=1}^{P} \beta_{CRF_p} * \overline{CRF_p} - \sum_{j=1}^{J} \beta_{SNP_j} * \overline{SNP_j}\right]}$$

prob($^{event|CRF,SNP}$): probability of presenting a coronary event given a combination of coronary risk factors (CRF) and genetic characteristics (SNP).

event$_i$: coronary event (fatal and non-fatal myocardial infarction or angina) in a 10-year period for an individual "i".

CRFp,i: value of each coronary risk factor "p" included in the equation for an individual "i". The list of coronary risk factors included in the model is shown in table A.

SNPj,i: number of risk alleles (0,1,2) for a specific genetic variant "j" included in the equation for an individual "i". The variants currently included in the model are shown in table B.

$\hat{S}$: mean survival free of coronary events at the population. This survival will be adapted to the regional or national rates.

exp: natural exponentiation.

$$\sum_{p=1}^{P} \beta_{CRF_p} * CRF_{p,i}:$$

where a.

$$\sum_{p=1}^{P}$$

summatory function along the P classical risk factors.

b. $\beta_{CRF_p}$ logarithm of hazard ratio corresponding to the classical coronary risk factor "p".

The values of the β for each coronary risk factor "p" are shown in table A. CRFp,i: value of each coronary risk factor "p" included in the equation for an individual "i".

$$\sum_{j=1}^{J} \beta_{SNP_j} * SNP_{j,i}:$$

where a.

$$\sum_{j=1}^{J}$$

summatory function along the J genetic variants.

$\beta_{SNP_j}$ logarithm of hazard ratio corresponding to the genetic variant "j". The possible range of values of the β for each genetic variant "j" is shown in table B.

SNPj,i: number of risk alleles (0,1,2) for a specific genetic variant "j" included in the equation for an individual "i".

$\overline{CRF_p}$: average value for the classical risk factor "p" in the population. This average value will be adapted to the regional or national prevalence.

$\overline{SNP_j}$: average risk allele number of copies for genetic variant "j" in the population. This average value will be adapted to the regional or national prevalence.

TABLE A

List of coronary risk factors included in the model, logarithm of hazard ratio, $\beta CRF_p$, for every classical risk factor by gender, range of the average values for the classical risk factor "p" in the population, and mean survival free of coronary events rate at the population ($\hat{S}$) (range of possible values).

| | CRFP | $\beta CRF_p$ for Men | $\beta CRF_p$ for Women | $\overline{CRF_p}$ |
|---|---|---|---|---|
| FRAMINGHAM (original or adaptation) | Age | 0.048 | 0.338 | 35-74 |
| | Age2 | 0 | −0.003 | |
| | Total cholesterol (mg/dL) | | | |
| | <160 | −0.659 | −0.261 | 0-30 |
| | 160-<200 | 0 | 0 | 0-30 |
| | 200-<240 | 0.177 | 0.208 | 0-30 |
| | 240-<280 | 0.505 | 0.244 | 0-30 |
| | ≥280 | 0.657 | 0.53 | 0-30 |
| | HDL Cholesterol (mg/dL) | | | |
| | <35 | 0.497 | 0.843 | 0-30 |
| | 35-<45 | 0.243 | 0.378 | 0-30 |
| | 45-<50 | 0 | 0.198 | 0-30 |
| | 50-<60 | −0.051 | 0 | 0-30 |
| | ≥60 | −0.487 | −0.430 | 0-30 |
| | Blood pressure | | | |
| | Optimal | −0.002 | −0.534 | 0-30 |
| | Normal | 0 | 0 | 0-30 |
| | Bordeline-High | 0.283 | −0.068 | 0-30 |
| | Hypertension I | 0.522 | 0.263 | 0-30 |
| | Hypertension II | 0.619 | 0.466 | 0-30 |
| | Diabetes | 0.428 | 0.597 | 0-30 |
| | Smoking | 0.523 | 0.292 | 0-60 |
| PROCAM | Age | 0.103 | — | 35-74 |
| | LDL-cholesterol (mg/dL) | 0.013 | — | 100-250 |
| | HDL-cholesterol (mg/dL) | −0.032 | — | 35-65 |
| | Triglycerides (mg/dL) | 0.317 | — | 100-200 |
| | Systolic blood pressure (mmHg) | 0.010 | — | 100-160 |
| | Family history of MI | 0.382 | — | 1-45 |
| | Diabetes | 0.399 | — | 0-30 |
| QRISK | Log(age/10) | 4.474 | 3.925 | 35-74 |
| | Total cholesterol/ HDL chol. | 0.001 | 0.001 | 2-10 |
| | Body mass index (kg/m2) | 0.015 | 0.022 | 22-32 |
| | Family history of premature CVD | 0.206 | 0.262 | 1-45 |
| | Smoking | 0.425 | 0.349 | 0-60 |
| | Townsend score of output area | 0.034 | 0.017 | −3-3 |
| | Systolic blood pressure (mmHg) | 0.005 | 0.004 | 100-160 |
| | Treatment for hypertension | 0.550 | 0.614 | 0-40 |
| | Interaction SBP*HTN treatment | −0.004 | −0.007 | — |
| | Mean Survival $\hat{S}$ | 0.951 (0.01-9.00) | 0.978 (0.01-9.00) | |

TABLE B

Variants currently included in the model, logarithm of hazard ratio (range of possible values), $\beta_{SNPj}$, and average risk allele number of copies (range of possible values), $\overline{SNP_j}$ for every genetic variant.

| SNPj | $\beta_{SNPj}$ | $\overline{SNP_j}$ |
|---|---|---|
| rs1333049 | 0.30010 (0-0.80) | 0.94 (0.3-2.8) |
| rs599839 | 0.16551 (0-0.60) | 1.54 (0.3-2.8) |
| rs17465637 | 0.12222 (0-0.60) | 1.44 (0.3-2.8) |
| rs501120 | 0.17395 (0-0.60) | 1.74 (0.3-2.8) |
| rs2943634 | 0.19062 (0-0.60) | 1.32 (0.3-2.8) |
| rs6922269 | 0.20701 (0-0.60) | 0.50 (0.3-2.8) |
| rs9982601 | 0.1823 (0-0.60) | 0.26 (0.3-2.8) |
| rs12526453 | 0.1133 (0-0.60) | 1.10 (0.3-2.8) |
| rs6725887 | 0.1570 (0-0.60) | 0.28 (0.3-2.8) |
| rs9818870 | 0.1398 (0-0.60) | 0.34 (0.3-2.8) |
| rs3184504 | 0.1222 (0-0.60) | 0.76 (0.3-2.8) |
| Other SNPs | 0.1200 (0-0.60) | 0.3-2.8 (0.3-2.8) |

Function 1b

This general equation can be used to calculate the coronary or cardiovascular risk using the risk factors and effects of the risk factors included and defined in the Framingham (the original and/or the adapted such as but not limited to REGICOR), PROCAM and QRISK functions:

$$prob(event_i \mid CRF_{p,i}, GSQ_{q,i}) = \frac{\exp\left[\sum_{p=1}^{P}\beta_{CRF_p}*CRF_{p,i} + \sum_{q=1}^{Q}\beta_{GSQ_{q,i}}*GSQ_{q,i} - \sum_{p=1}^{P}\beta_{CRF_p}*\overline{CRF_p} - \sum_{q=1}^{Q}\beta_{GSQ_q}*\overline{GSQ_Q}\right]}{1-\hat{S}}$$

wherein prob($^{event \mid CRF,GSQ}$): probability of presenting a coronary event given a combination of coronary risk factors (CRF) and genetic characteristics (GSQ).

eventi: coronary event (fatal and non-fatal myocardial infarction or angina) in a 10-year period for an individual "i".

CRFp,i: value of each coronary risk factor "p" included in the equation for an individual "i". The list of coronary risk factors included in the model is shown in table C.

$GSQ_{q,i}$: genetic score quintile "q" according to the distribution of the number of risk alleles (0,1,2) for the genetic variants included in the equation at the population level for an individual "i". The variants currently included in the model are shown in table D.

$\hat{S}$: mean survival free of coronary events at the population. This survival will be adapted to the regional or national rates.

exp: natural exponentiation.

$$\sum_{p=1}^{P}\beta_{CRF_p}*CRF_{p,i}:$$

where
a.

$$\sum_{p=1}^{P}$$

summatory function along the P classical risk factors.

$\beta_{CRF_p}$ logarithm of hazard ratio corresponding to the classical coronary risk factor "p". The values of the β for each coronary risk factor "p" are shown in table C.

CRFp,i: value of each coronary risk factor "p" included in the equation for an individual "i".

$$\sum_{q=1}^{Q} \beta_{GSQ_q} * GSQ_{q,i}:$$

where
a.

$$\sum_{q=1}^{Q}$$

summatory function along the Q (5) quintiles.

βGSQq: logarithm of hazard ratio corresponding to different genetic score quintiles (QSQ) "q". The possible range of values of the β for each quintile "q" is shown in table D.

GSQq,i: genetic score quintile "q" according to the distribution of the number of risk alleles (0,1,2) for the genetic variants included in the equation at the population level for an individual "i".

$\overline{CRF_p}$: average value for the classical risk factor "p" in the population. This average value will be adapted to the regional or national prevalence.

$\overline{GSQ_Q}$: values from 1 to 5 of the different quintiles for the genetic score quintile "q" in the population

TABLE C

List of coronary risk factors included in the model, logarithm of hazard ratio, $\beta CRF_p$, for every classical risk factor by gender, range of the average values for the classical risk factor "p" in the population, and mean survival free of coronary events rate at the population ($\hat{S}$) (range of possible values).

| | CRFP | $\beta CRF_p$ for Men | $\beta CRF_p$ for Women | $\overline{CRF_p}$ |
|---|---|---|---|---|
| FRAMINGHAM (original or adaptation) | Age | 0.048 | 0.338 | 35-74 |
| | Age2 | 0 | −0.003 | |
| | Total cholesterol (mg/dL) | | | |
| | <160 | −0.659 | −0.261 | 0-30 |
| | 160-<200 | 0 | 0 | 0-30 |
| | 200-<240 | 0.177 | 0.208 | 0-30 |
| | 240-<280 | 0.505 | 0.244 | 0-30 |
| | ≥280 | 0.657 | 0.53 | 0-30 |
| | HDL Cholesterol (mg/dL) | | | |
| | <35 | 0.497 | 0.843 | 0-30 |
| | 35-<45 | 0.243 | 0.378 | 0-30 |
| | 45-<50 | 0 | 0.198 | 0-30 |
| | 50-<60 | −0.051 | 0 | 0-30 |
| | ≥60 | −0.487 | −0.430 | 0-30 |
| | Blood pressure | | | |
| | Optimal | −0.002 | −0.534 | 0-30 |
| | Normal | 0 | 0 | 0-30 |
| | Bordeline-High | 0.283 | −0.068 | 0-30 |
| | Hypertension I | 0.522 | 0.263 | 0-30 |

TABLE C-continued

List of coronary risk factors included in the model, logarithm of hazard ratio, $\beta CRF_p$, for every classical risk factor by gender, range of the average values for the classical risk factor "p" in the population, and mean survival free of coronary events rate at the population ($\hat{S}$) (range of possible values).

| | CRFP | $\beta CRF_p$ for Men | $\beta CRF_p$ for Women | $\overline{CRF_p}$ |
|---|---|---|---|---|
| | Hypertension II | 0.619 | 0.466 | 0-30 |
| | Diabetes | 0.428 | 0.597 | 0-30 |
| | Smoking | 0.523 | 0.292 | 0-60 |
| PROCAM | Age | 0.103 | — | 35-74 |
| | LDL-cholesterol (mg/dL) | 0.013 | — | 100-250 |
| | HDL-cholesterol (mgldL) | −0.032 | — | 35-65 |
| | Triglycerides (mg/dL) | 0.317 | — | 100-200 |
| | Systolic blood pressure (mmHg) | 0.010 | — | 100-160 |
| | Family history of MI | 0.382 | — | 1-45 |
| | Diabetes | 0.399 | — | 0-30 |
| QRISK | Log(age/10) | 4.474 | 3.925 | 35-74 |
| | Total cholesterol/ HDL chol. | 0.001 | 0.001 | 2-10 |
| | Body mass index (kg/m2) | 0.015 | 0.022 | 22-32 |
| | Family history of premature CVD | 0.206 | 0.262 | 1-45 |
| | Smoking | 0.425 | 0.349 | 0-60 |
| | Townsend score of output area | 0.034 | 0.017 | −3-3 |
| | Systolic blood pressure (mmHg) | 0.005 | 0.004 | 100-160 |
| | Treatment for hypertension | 0.550 | 0.614 | 0-40 |
| | Interaction SBP*HTN treatment | −0.004 | −0.007 | — |
| | Mean Survival $\hat{S}$ | 0.951 (0.01-9.00) | 0.978 (0.01-9.00) | |

TABLE D

Genetis Score Quintiles (GSQq) definition according to the number of risk alleles and logarithm of hazard ratio (range of possible values), $\beta GSQq$, for the genetic score quintiles.

| GSQq | $\beta GSQq$ |
|---|---|
| 1 (0-6/9 risk alleles) | 0 |
| 2 (7/10 risk alleles) | 0.2 (0-0.8) |
| 3 (9/11 risk alleles) | 0.4 (0-1.2) |
| 4 (10/12 risk alleles) | 0.6 (0-1.6) |
| 5 (11/12-22 risk alleles) | 0.8 (0-2.0) |

These quintiles will be built according to the allele frequencies of the following genetic variants (see table 1) (rs1333049, rs599839, rs17465637, rs501120, rs2943634, rs6922269, rs9982601, rs12526453, rs6725887, rs9818870, rs3184504).

Function 1c

The coronary or cardiovascular risk will be calculated using the following equations using the SCORE risk function:

First step: compute linear combination of risk factors $$w_i = \beta_{chol} * (cholesterol_i - 6) + \beta_{SPB} * (SBP_i - 120) +$$

$$\beta_{smoker} * current_i + \sum_{j=1}^{J} \beta_{SNP_j} * (SNP_{i,j} - \overline{SNP_{i,j}})$$

where cholesteroli: cholesterol level for the individual "i" in mmol/L.

βchol: logarithm of hazard ratio corresponding to the cholesterol (Table E).

SBPi: systolic blood pressure for the individual "i" in mmHg.

βSBP: logarithm of hazard ratio corresponding to systolic blood pressure (Table E).

currenti: current smoking status for the individual "i" (1: current, 0: former/never).

βsmoker: logarithm of hazard ratio corresponding to systolic blood pressure (Table E).

$$\sum_{j=1}^{J} \beta_{SNP_j} * (SNP_{i,j} - \overline{SNP_{i,j}}):$$

$$\sum_{j=1}^{J}$$

summatory function along the J genetic variants.

$\beta_{SNP_j}$ logarithm of hazard ratio corresponding to the genetic variant "j". The possible range of values of the β for each genetic variant "j" is shown in table B.

SNPj,i: number of risk alleles (0,1,2) for a specific genetic variant "j" included in the equation for an individual "i".

$\overline{SNP_j}$: average risk allele number of copies for genetic variant "j" in the population. This average value will be adapted to the regional or national prevalence.

Second step: compute baseline survival.

$$S_0(age)=\exp\{-\exp(\alpha)*(age-20)^p\}$$

$$S_0(age+10)=\exp\{-\exp(\alpha)*(age-10)^p\}$$

where

α, p: shape and scale parameters of the weibull distribution. Their values are shown in Table F (parameters)

exp: natural exponentiation

Third step: compute 10 years survival $$S(age)=\{S_0(age)\}^{\exp(w)}$$

$$S(age+10)=\{S_0(age+10)\}^{\exp(w)}$$

$$S_{10}(age)=S(age+10)/S(age)$$

Fourth step: compute probability of having the event during the 10 years follow-up.

$$Risk_{10}(age)=1-S_{10}(age)$$

Fifth step: compute the probability of having a cardiovascular event during the 10 years follow-up as the sum of coronary and non-coronary cardiovascular risk.

$$CVDRisk_{10}=[CHDRisk_{10}(age)]+[Non-CHDRisk_{10}(age)]$$

TABLE E

|  | CHD | Non-CHD CVD |
|---|---|---|
| Current smoker, βsmoker | 0.71 | 0.63 |
| Cholesterol (mmol/L), βchol | 0.24 | 0.02 |
| Systolic blood pressure (mmHg), βSBP | 0.018 | 0.022 |

CHD: coronary heart disease
CVD: cardiovascular disease

TABLE F

|  |  | CHD | | Non-CHD CVD | |
|---|---|---|---|---|---|
| Country |  | A | p | α | p |
| Low risk | Men | −22.1 | 4.71 | −26.7 | 5.64 |
|  | Women | −29.8 | 6.36 | −31.0 | 6.62 |
| High risk | Men | −21.0 | 4.62 | −25.7 | 5.47 |
|  | Women | −28.7 | 6.23 | −30.0 | 6.42 |

CHD: coronary heart disease
CVD: cardiovascular disease

Surprisingly, the combination of SNP markers included in the present invention and set forth in table 1 and using the functions described in functions 1a to 1c above have proved to obtain a higher validity and a superior validation in predicting CVD and/or CVD complications than that obtained using the classical risk factors and using the functions nowadays in use or published functions including genetic information. Moreover, the reclassification was also improved.

Computer-Implemented Means of the Invention

Another object of the present invention is the provision of a computer program or computer-readable media containing means for carrying out any of the methods of the invention. Computer implementation can be achieved using a computer program providing instructions in a computer readable form. The computer would collect the data, analyze the data as in accordance with the methods described herein, and then provide a result of the analysis. Thus, in another embodiment, the invention relates to a computer program or a computer-readable media containing means for carrying out a method of the invention.

Different types of computer language can be used to provide instructions in a computer readable form. For example, the computer program can be written using languages such as C, C++, Microsoft C#, Microsoft Visual Basic, FORTRAN, PERL, HTML, JAVA, S, UNIX or LINUX shell command languages such as C shell script, and different dialects of such languages. "R," an S language dialect, is an example of a dialect with attributes facilitating analyses like those presented here (see http://cran.us.r-project.org).

Different types of computers can be used to run a program for performing analysis techniques described herein. Computer programs for performing analysis techniques described herein can be run on a computer having sufficient memory and processing capability. An example of a suitable computer is one having an Intel Pentium (g)-based processor of 200 MHZ or greater, with 64 MB or more main memory. Equivalent and superior computer systems are well known in the art. Standard operating systems can be employed for different types of computers. Examples of operating systems for an Intel Pentium (2)-based processor includes the Microsoft Windows™ family such as Windows NT, Windows XP, and Windows 2000 and LINUX. Examples of operating systems for Apple computers include OSX, UNIX and LINUX operating systems. Other computers and their operating systems are well known in the art. In different embodiments, the R language is used on an Intel-based computer with 4 GB ram dual 866 MHz Pentium m processors running the LINUX-operating system or an IBM computer running the AIX operating system with an Intel-based computer running the Windows NT or XP operating system as an x-windows terminal.

Kits of the Invention

The invention further relates to a kit for determining the presence of the polymorphic markers used in the methods of the invention, comprising wholly or in part: amplification reagents for amplifying nucleic acid fragments containing SNP markers and detection reagents for genotyping SNP markers.

Thus, in another aspect, the invention relates to a kit comprising reagents for detecting the identity of the polymorphisms at positions 27 within the nucleic acid sequence of SEQ ID NO:1 to 10 as defined in Table 1 above.

A person skilled in the art will recognize that, based on the SNP and associated sequence information disclosed herein, detection reagents can be developed and used to assay any SNP of the present invention individually or in combination, and such detection reagents can be readily incorporated into one of the established kit or system formats which are well known in the art. The kits may further comprise a questionnaire of classical clinical factors.

The terms "kits" and "systems", as used herein in the context of SNP detection reagents, are intended to refer to objects or devices such as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). Accordingly, the present invention further provides SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more SNPs of the present invention. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment of the present invention, kits are provided which contain the necessary reagents to carry out one or more assays to detect one or more SNPs disclosed herein. In a preferred embodiment of the present invention, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is a SNP of the present invention. In some kits/systems, the allele-specific probes are immobilized to a substrate such as an array or bead. For example, the same substrate can comprise allele-specific probes for detecting at least 1; 10; 100; 1000; 10,000; 100,000; 500,000 (or any other number in-between) or substantially all of the SNPs disclosed herein.

Preferably, the kit comprises several oligonucleotides that will hybridize specifically to the nucleic acid sequences defined in Table 1 or to sequences flanking said regions. These oligonucleotides will enable specific amplification of the polynucleotide wherein the polymorphic position is to be assessed from a human genomic DNA or cDNA template, using PCR. Most preferably, these oligonucleotides will also enable specific genotyping of these polymorphic sites by acting as primers, probes, or ligation substrates that enable differentiation of polymorphic alleles. Alternatively, these oligonucleotides may be suitable for use in methods that do not depend on prior amplification of the starting DNA, such as Invader assays and ligation-based detection methods. Preferably the oligonucleotides or other kit components will include a detectable label, e.g., a fluorescent label, enzyme label, light scattering label, mass label, or other label. Alternatively, detection may be achieved by RFLP methods. In addition, the kit may include a plurality of different nucleic acid sequences allowing detection of nucleic acid sequences or gene products corresponding to different polymorphisms as defined in Table 1. The kit may also optionally contain instructions for use, which can include a listing of the polymorphisms correlating with a particular treatment or treatments for a disease or diseases and/or a statement or listing of the diseases for which a particular polymorphism or polymorphisms correlates with a treatment efficacy and/or safety.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separately from the substrate and then affixed to the substrate. In one embodiment, the microarray is prepared and used according to the methods described in U.S. Pat. No. 5,837,832, Chee et al, PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), all of which are incorporated herein in their entirety by reference. In other embodiments, such arrays are produced by the methods described by Brown et al., U.S. Pat. No. 5,807,522.

Nucleic acid arrays are reviewed in the following references: Zammatteo et al., "New chips for molecular biology and diagnostics", Biotechnol Annu Rev. 2002; 8:85-101; Sosnowski et al., "Active microelectronic array system for DNA hybridization, genotyping and pharmacogenomic applications", Psychiatr Genet. 2002 December; 12(4): 181-92; Heller, "DNA microarray technology: devices, systems, and applications", Annu Rev Biomed Eng. 2002; 4: 129-53. Epub 2002 Mar. 22; Kolchinsky et al., "Analysis of SNPs and other genomic variations using gel-based chips", Hum Mutat. 2002 April; 19(4):343-60; and McGall et al., "High-de genechip oligonucleotide probe arrays", Adv Biochem Eng Biotechnol. 2002; 77:21-42.

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array. A microarray can be composed of a large number of unique, single-stranded polynucleotides fixed to a solid support. Typical polynucleotides are preferably about 6-60 nucleotides in length, more preferably about 15-30 nucleotides in length, and most preferably about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length. The microarray or detection kit can contain polynucleotides that cover the known 5' or 3' sequence of the target SNP site, sequential polynucleotides that cover the full-length sequence of a gene/transcript; or unique polynucleotides selected from particular areas along the length of a target gene/transcript sequence, particularly areas corresponding to one or more SNPs disclosed herein. Polynucleotides used in the microarray or detection kit can be specific to a SNP or SNPs of interest (e.g., specific to a particular SNP allele at a target SNP site, or specific to particular SNP alleles at multiple different SNP sites), or specific to a polymorphic gene/transcript or genes/transcripts of interest.

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions may be preferable when using, for example, nucleic acid arrays of allele-specific probes for SNP detection. Such high stringency conditions are described in the preceding section, and are well known to those skilled in the art and can be found in, for example, Current Protocols in Molecular Biology, John Wiley and Sons, N.Y. (1989), 6.3.1-6.3.6.

In other embodiments, the arrays are used in conjunction with chemiluminescent detection technology. The following patents and patent applications, which are all hereby incorporated by reference, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871,938, 5,843,681, 5,800,999, and 5,773,628 describe methods and compositions of dioxetane for performing chemiluminescent detection; and U.S. published application US2002/0110828 discloses methods and compositions for microarray controls.

In one embodiment of the invention, a nucleic acid array can comprise an array of probes of about 15-25 nucleotides in length. In further embodiments, a nucleic acid array can comprise any number of probes, in which at least one probe is capable of detecting one or more SNPs disclosed in Tables 1-10 and/or at least one probe comprises a fragment of one of the sequences selected from the group consisting of those disclosed herein, and sequences complementary thereto, said fragment comprising at least about 8 consecutive nucleotides, preferably 10, 12, 15, 16, 18, 20, more preferably 22, 25, 30, 40, 47, 50, 55, 60, 65, 70, 80, 90, 100, or more consecutive nucleotides (or any other number in-between) and containing (or being complementary to) a SNP. In some embodiments, the nucleotide complementary to the SNP site is within 5, 4, 3, 2, or 1 nucleotide(s) from the center of the probe, more preferably at the center of said probe.

A polynucleotide probe can be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

The uses of the kits according to the invention typically involve incubating a test sample of nucleic acids with an array comprising one or more probes corresponding to at least one SNP position of the present invention, and assaying for binding of a nucleic acid from the test sample with one or more of the probes. Conditions for incubating a SNP detection reagent (or a kit/system that employs one or more such SNP detection reagents) with a test sample vary. Incubation conditions depend on such factors as the format employed in the assay, the detection methods employed, and the type and nature of the detection reagents used in the assay. One skilled in the art will recognize that any one of the commonly available hybridization, amplification and array assay formats can readily be adapted to detect the SNPs disclosed herein.

A SNP detection kit/system of the present invention may include components that are used to prepare nucleic acids from a test sample for the subsequent amplification and/or detection of a SNP-containing nucleic acid molecule. Such sample preparation components can be used to produce nucleic acid, including DNA and/or RNA, extracts from any bodily fluids. In a preferred embodiment of the invention, the bodily fluid is blood, saliva or buccal swabs. The test samples used in the above-described methods will vary based on such factors as the assay format, nature of the detection method, and the specific tissues, cells or extracts used as the test sample to be assayed. Methods of preparing nucleic acids are well known in the art and can be readily adapted to obtain a sample that is compatible with the system utilized. In yet another form of the kit in addition to reagents for preparation of nucleic acids and reagents for detection of one of the SNPs of this invention, the kit may include a questionnaire inquiring about non-genetic clinical factors such as known to be associated with CVD such as age, race, sex, body mass index, blood pressure, smoking status, alcohol consumption history, smoking history, exercise history, diet, family history of cardiovascular disease, total cholesterol, low density lipoprotein (LDL)- or high density lipoprotein(HDL)-cholesterol levels, systolic blood pressure, diastolic blood pressure, history of heart failure, diabetes, renal insufficiency, or left ventricular hypertrophy.

Another form of kit contemplated by the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow the user to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more SNPs of the present invention, one or more containers which contain wash reagents (such as phosphate buffered saline, Tris-buffers, etc.), and one or more containers which contain the reagents used to reveal the presence of the bound probe or other SNP detection reagents. The kit can optionally further comprise compartments and/or reagents for, for example, nucleic acid amplification or other enzymatic reactions such as primer extension reactions, hybridization, ligation, electrophoresis (preferably capillary electrophoresis), mass spectrometry, and/or laser-induced fluorescent detection. The kit may also include instructions for using the kit. Exemplary compartmentalized kits include micro fluidic devices known in the art (see, e.g., Weigl et al., "Lab-on-a-chip for drug development", Adv Drug Deliv Rev. 2003 Feb. 24; 55(3):349-77). In such microfluidic devices, the containers may be referred to as, for example, microfluidic "compartments", "chambers", or "channels".

Microfluidic devices, which may also be referred to as "lab-on-a-chip" systems, biomedical micro-electro-mechanical systems (bioMEMs), or multicomponent integrated systems, are exemplary kits/systems of the present invention for analyzing SNPs. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more SNPs of the present invention. One example of a microfluidic system is disclosed in U.S. Pat. No. 5,589,136, which describes the integration of PCR amplification and capillary electrophoresis in chips. Exemplary microfluidic systems comprise a pattern of microchannels designed onto a glass, silicon, quartz, or plastic wafer included on a microchip. The movements of the samples may be controlled by electric, electroosmotic or hydrostatic forces applied across different areas of the microchip to create functional microscopic valves and pumps with no moving parts. Varying the voltage can be used as a means to control the liquid flow at intersections between the micro-machined channels and to change the liquid flow rate for pumping across different sections of the microchip. See, for example, U.S. Pat. No. 6,153,073, Dubrow et al, and U.S. Pat. No. 6,156,181, Parce et al.

For genotyping SNPs, a microfluidic system may integrate, for example, nucleic acid amplification, primer extension, capillary electrophoresis, and a detection method such as laser induced fluorescence detection.

Methods and Kits for the Detection of Predisposition to Develop the Classical Risk Factors of CVD Another object of the present invention is a particular combination of single nucleotide polymorphism (SNP) markers associated with the predisposition to develop the classical risk factors of CVD and/or the classical risk factors of CVD complications including, but not limited to, myocardial infarction, stroke, angina pectoris, transient ischemic attacks, congestive heart failure, aortic aneurysm and death. Classical risk factors of CVD and/or CVD complications include, but are not limited to, diabetes mellitus, high total cholesterol levels, high LDL-cholesterol levels, low HDL-cholesterol levels, high triglyceric levels, obesity, addiction to smoking, hypertension and thrombosis.

Surprisingly, the specific combination of SNP markers included in the present invention as set forth in table 2 has proved to obtain a higher capability to predict the development of diabetes mellitus than that obtained using the methods nowadays in use and/or by the consideration of any single SNP set forth in table 2 and/or the consideration of a subset of the SNP set forth in table 2.

TABLE 2

| SNP | GENE | Risk allele |
| --- | --- | --- |
| rs4506565 | TCF7L2 | T |
| rs7903146 | TCF7L2 | T |
| rs12255372 | TCF7L2 | T |
| rs4132670 | TCF7L2 | T |
| rs734312 | WFS1 | A |
| rs10811661 | CDKN2B | C |
| rs7756992 | CDKAL1 | G |
| rs1111875 | HHEX | A |
| rs7923837 | HHEX | A |
| rs9465871 | CDKAL1 | C |
| rs4430796 | TCF2 | G |
| rs564398 | CDKN2B | G |
| rs5219 | KCNJ11 | C |
| rs13266634 | SLC30A8 | T |
| rs5215 | KCNJ11 | C |
| rs1801282 | PPARG | G |
| rs7501939 | TCF2 | C |
| rs1801208 | WSF1 | G |
| rs2383208 | CDKN2B | G |

Thus, in another aspect, the invention relates to a method for the determination whether a subject has an altered risk of having diabetes mellitus which comprises determining in a biological sample from said subject the presence of the polymorphisms shown in Table 2, wherein the presence of the risk alleles is indicative of an increased risk of developing diabetes mellitus.

Surprisingly, the specific combination of SNP markers included in the present invention and set forth in table 3 has proved to obtain a higher capability to predict the development of high total cholesterol levels than that obtained using the methods nowadays in use and/or by the consideration of any single SNP set forth in table 3 and/or the consideration of a subset of the SNP set forth in table 3.

TABLE 3

| SNP | GENE | Risk allele |
| --- | --- | --- |
| rs12664989 | ESR1 | C |
| rs1801177 | LPL | A |
| rs268 | LPL | G |
| rs328 | LPL | G |

Thus, in another aspect, the invention relates to a method for the determination whether a subject has an altered risk of having high total cholesterol levels which comprises determining in a biological sample from said subject the presence of the polymorphisms shown in Table 3, wherein the presence of the risk alleles is indicative of an increased risk of developing high total cholesterol levels.

Surprisingly, the specific combination of SNP markers included in the present invention and set forth in table 4 has proved to obtain a higher capability to predict the development of high LDL-cholesterol levels than that obtained using the methods nowadays in use and/or by the consideration of any single SNP set forth in table 4 and/or the consideration of a subset of the SNP set forth in table 4.

TABLE 4

| SNP | GENE | Risk allele |
| --- | --- | --- |
| rs4420638 | APOC1 | G |
| rs287479 | chr13 | A |
| rs11591147 | PCSK9 | T |
| rs599839 | PSRC1 | G |
| rs780094 | GCKR | T |
| rs12664989 | ESR1 | C |
| rs9322331 | ESR1 | T |
| rs7412 | APOE | C |
| rs693 | APOB | T |

Thus, in another aspect, the invention relates to a method for the determination whether a subject has an altered risk of having high LDL-cholesterol levels which comprises determining in a biological sample from said subject the presence of the polymorphisms shown in Table 4, wherein the presence of the risk alleles is indicative of an increased risk of developing high LDL-cholesterol levels.

Surprisingly, the specific combination of SNP markers included in the present invention and set forth in table 5 has proved to obtain a higher capability to predict the development of low HDL-cholesterol levels than that obtained using the methods nowadays in use and/or by the consideration of any single SNP set forth in table 5 and/or the consideration of a subset of the SNP set forth in table 5.

TABLE 5

| SNP | GENE | Risk allele |
| --- | --- | --- |
| rs2066715 | ABCA1 | T |
| rs2066718 | ABCA1 | A |
| rs2230808 | ABCA1 | A |
| rs505717 | ZNF568 | G |
| rs569371 | Chr19 | G |
| rs3734678 | PDSS2 | C |
| rs5882 | CETP | G |
| rs1800775 | CETP | C |
| rs708272 | CETP | T |
| rs7412 | APOE | T |
| rs328 | LPL | G |
| rs7007797 | LPL | G |
| rs2230806 | ABCA1 | A |

Thus, in another aspect, the invention relates to a method for the determination whether a subject has an altered risk of having high HDL-cholesterol levels which comprises determining in a biological sample from said subject the presence of the polymorphisms shown in Table 5, wherein the presence of the risk alleles is indicative of an increased risk of developing high HDL-cholesterol levels.

Surprisingly, the specific combination of SNP markers included in the present invention and set forth in table 6 has proved to obtain a higher capability to predict the development of high triglyceride levels than that obtained using the methods nowadays in use and/or by the consideration of any single SNP set forth in table 6 and/or the consideration of a subset of the SNP set forth in table 6.

TABLE 6

| SNP | GEN | Risk allele |
| --- | --- | --- |
| rs7007075 | Chr8 | T |
| rs9322331 | ESR1 | T |
| rs780094 | GCKR | G |
| rs7007797 | LPL | G |
| rs4420638 | APOC1 | G |
| rs662799 | APOA5 | G |
| rs6589566 | APOA5 | G |
| rs651821 | APOA5 | C |
| rs2072560 | APOA5 | T |
| rs693 | APOB | T |
| rs1800775 | CETP | C |
| rs328 | LPL | G |
| rs1801177 | LPL | A |
| rs268 | LPL | G |
| rs320 | LPL | G |
| rs2230806 | ABCA1 | A |
| rs7412 | APOE | C |

Thus, in another aspect, the invention relates to a method for the determination whether a subject has an altered risk of having high triglyceride levels which comprises determining in a biological sample from said subject the presence of the polymorphisms shown in Table 6, wherein the presence of the risk alleles is indicative of an increased risk of developing high triglyceride levels.

Surprisingly, the specific combination of SNP markers included in the present invention and set forth in table 7 has proved to obtain a higher capability to predict the development of obesity than that obtained using the methods nowadays in use and/or by the consideration of any single SNP set forth in table 7 and/or the consideration of a subset of the SNP set forth in table 7.

TABLE 7

| SNP | GENE | Risk allele |
| --- | --- | --- |
| rs10510422 | PPARG | C |
| rs10510423 | PPARG | G |
| rs299629 | PPARG | G |
| rs2938392 | PPARG | T |
| rs709157 | PPARG | A |
| rs963163 | PPARG | C |
| rs6602024 | PFKP | A |
| rs2229616 | MC4R | A |
| rs52820871 | MC4R | C |
| rs1106683 | intergenic | A |
| rs7566605 | INSIG2 | C |
| rs4471028 | GDAP1 | G |
| rs1121980 | FTO | T |
| rs1421085 | FTO | C |
| rs7193144 | FTO | C |
| rs8050136 | FTO | A |
| rs9930506 | FTO | G |

TABLE 7-continued

| SNP | GENE | Risk allele |
|---|---|---|
| rs9939609 | FTO | A |
| rs9940128 | FTO | A |
| rs10484922 | ESR1 | T |
| rs3778099 | ESR1 | C |
| rs3853250 | ESR1 | C |
| rs6902771 | ESR1 | T |
| rs851982 | ESR1 | C |
| rs9322361 | ESR1 | G |
| rs1044498 | ENPP1 | C |
| rs10490628 | CCDC93 | A |
| rs3771942 | CCDC93 | C |
| rs9284719 | CCDC93 | T |
| rs4994 | ADRB3 | C |
| rs1042464 | ADIPOQ | T |

Thus, in another aspect, the invention relates to a method for the determination whether a subject has an altered risk of developing obesity which comprises determining in a biological sample from said subject the presence of the polymorphisms shown in Table 7, wherein the presence of the risk alleles is indicative of an increased risk of developing obesity.

Surprisingly, the specific combination of SNP markers included in the present invention and set forth in table 8 has proved to obtain a higher capability to predict the development of smoking addiction than that obtained using the methods nowadays in use and/or by the consideration of any single SNP set forth in table 8 and/or the consideration of a subset of the SNP set forth in table 8.

TABLE 8

| SNP | GEN | Risk allele |
|---|---|---|
| rs4142041 | CTNNA3 | G |
| rs6474413 | CHRNB3 | C |
| rs1044397 | CHRNA4 | A |

Thus, in another aspect, the invention relates to a method for the determination whether a subject has an altered risk of developing smoking addiction which comprises determining in a biological sample from said subject the presence of the polymorphisms shown in Table 8, wherein the presence of the risk alleles is indicative of an increased risk of developing smoking addiction.

Surprisingly, the specific combination of SNP markers included in the present invention and set forth in table 9 have proved to obtain a higher capability to predict the development of hypertension than that obtained using the methods nowadays in use and/or by the consideration of any single SNP set forth in table 9 and/or the consideration of a subset of the SNP set forth in table 9.

TABLE 9

| SNP | GEN | Risk allele |
|---|---|---|
| rs11739136 | KCNMB1 | T |
| rs4762 | AGT | T |
| rs699 | AGT | C |
| rs4343 | ACE | G |
| rs4961 | ADD1 | T |
| rs2484294 | ADRB1 | G |
| rs1042711 | ADRB2 | C |
| rs17778257 | ADRB2 | T |
| rs1042714 | ADRB2 | G |
| rs1800888 | ADRB2 | T |
| rs1801704 | ADRB2 | C |

TABLE 9-continued

| SNP | GEN | Risk allele |
|---|---|---|
| rs2933249 | AGTR1 | T |
| rs275652 | AGTR1 | C |
| rs387967 | AGTR1 | C |
| rs5186 | AGTR1 | C |
| rs11091046 | AGTR2 | A |
| rs1799983 | NOS3 | T |
| rs1800779 | NOS3 | G |
| rs1800780 | NOS3 | G |
| rs1800782 | NOS3 | T |
| rs1800783 | NOS3 | A |
| rs2070744 | NOS3 | C |
| rs867225 | NOS3 | A |

Thus, in another aspect, the invention relates to a method for the determination whether a subject has an altered risk of developing hypertension which comprises determining in a biological sample from said subject the presence of the polymorphisms shown in Table 9, wherein the presence of the risk alleles is indicative of an increased risk of developing hypertension.

Surprisingly, the specific combination of SNP markers included in the present invention and as set out in table 10 have proved to obtain a higher capability to predict the development of thrombosis than that obtained using the methods nowadays in use and/or by the consideration of any single SNP set forth in table 10 and/or the consideration of a subset of the SNP set forth in table 10.

TABLE 10

| SNP | inclos | GEN | Risk allele |
|---|---|---|---|
| rs234706 | 1 | CBS | A |
| rs6025 | 1 | F5 | A |
| rs6064 | 1 | F7 | A |
| rs2070011 | 1 | FGA | A |
| rs1800789 | 1 | FGB | A |
| rs1764391 | 1 | GJA4 | T |
| rs1062535 | 0 | ITGA2 | A |
| rs1126643 | 1 | ITGA2 | T |
| rs5918 | 1 | ITGB3 | C |
| rs1801131 | 1 | MTHFR | C |
| rs1801133 | 1 | MTHFR | T |
| rs11178 | 1 | SERPINE1 | C |
| rs2227631 | 1 | SERPINE1 | G |
| rs2228262 | 1 | THBS1 | G |
| rs1866389 | 1 | THBS4 | G |
| rs7007329 | 1 | PLAT | C |
| rs917859 | 1 | VWF | A |

Thus, in another aspect, the invention relates to a method for the determination whether a subject has an altered risk of developing thrombosis which comprises determining in a biological sample from said subject the presence of the polymorphisms shown in Table 10, wherein the presence of the risk alleles is indicative of an increased risk of developing thrombosis.

Another object of the present invention is a method for estimating the predisposition to develop the classical risk factors of CVD and/or the classical risk factors of CVD complications including, but not limited to, diabetes mellitus, high total cholesterol levels, high LDL-cholesterol levels, low HDL-cholesterol levels, high triglyceric levels, obesity, addiction to smoking, hypertension and thrombosis, comprising the detection of the presence of SNP markers set for in tables 2 through 10.

To calculate the genetic risk the number of risk alleles will be counted that an individual carries in the different genetic variants associated with each metabolic pathway or risk factor. The higher the number of risk alleles present, the higher is the risk to develop each risk factor.

Those skilled in the art will readily recognize that the analysis of the nucleotides present in the SNP markers included in table 2-10 in an individual's nucleic acid can be done by any method or technique capable of determining nucleotides present in a polymorphic site. It is obvious in the art that the nucleotides present in SNP markers can be determined from either nucleic acid strand or from both strands. The detection of the presence of the SNP markers included in tables 2-10 is done from a biological sample of the subject. The biological sample can be any possible sample containing nucleic acid, preferably blood, cells or cell sub fractions (being the cells isolated from blood), saliva, urine, biopsy specimen and/or tissue specimen.

The invention further relates to a kit for determining the presence of the SNP markers comprising wholly or in part: amplification reagents for amplifying nucleic acid fragments containing SNP markers, detection reagents for genotyping SNP markers and interpretation software for data analysis and risk assessment.

A further object of the present invention are the functions to calculate the predisposition to develop the classical risk factors of CVD and/or the classical risk factors of CVD complications considering the particular combination of single nucleotide polymorphism (SNP) markers associated with such predisposition.

Example 1

Design of the Study

This is a case—control study with information in silico proceeding from the Wellcome Trust Case Control Consortium (WTCCC)]. The cases (N=1.988) were selected from the first phase of the WTCCC study. As it is described in the original study, coronary heart disease cases presented precedents myocardial infarction or coronary revascularization (including coronary bypass coronary or coronary angioplastia) before 66 years old. The controls were 2.674 subjects from blood donors [UK Blood Services Controls (NBS)], included in the project WTCCC.

The SNPs listed in table 1A were analyzed for this example. The SNPs analysed are: rs 17465637, rs 6725887, rs 9818870, rs 12526453, rs 6922269, rs 1333049, rs 501120 (by analyzing its LD rs1746048), rs 17228212, and rs 9982601. For each of the variants an allele of risk defined, that is to say that nucleotide that when present awards a major risk of suffering a coronary event.

To calculate the genetic risk punctuation, the accumulated number of risk allele risk from those nine SNPs present in each individual was considered. For each of the variants studied, every individual can have 0, 1 or 2 alleles of risk. On having calculated the summatory of risk allele accumulated in the set of the selected variants (n=9), for each individual a score that could go from 0 to 18 was given (low score=low risk, high score=high risk).

To consider the additive effect of the set of the different genetic variants, first the distribution of the accumulated number of risk alleles was analyzed in cases and controls, and the difference of the average of the punctuation of genetic risk between cases and controls was compared by means of the Student's t test.

Afterwards, the logistic regression was used for the estimation of the association between the genetic risk punctuation and the risk of myocardial infarction and several analyses were performed:

a) First, this variable of genetic risk was considered as a categorical variable. As reference group we consider that group of persons carrying 7 of the risk alleles, which is the value nearest to the median in controls and for being the group with the highest number of individuals that allows to obtain the most precise risk estimators. The OR (odd ratio) were estimated for every category of the genetic risk punctuation (Group of carriers of 8 alleles vs carriers of 7 alleles; carriers of 9 alleles vs 7; carriers of 6 alleles vs 7; and so on);
b) Second, the OR was calculated by increase of allele of risk taking this variable as a continues variable and assuming that the risk is constant for increase of allele in the range of observed values, and it was analyzed whether the association between number of alleles and the risk of myocardial infarction were lineal.
c) Third, the analysis explained in the paragraph a) was repeated but defining the groups based on the quintiles of genetic risk punctuation obtained in the control group and taking as reference the first quintile.

Also it was analyzed if there were interactions between the genetic variants of interest to determine if the effect of the combination of the same ones was superior to the additive.

For all these analyses a value of $p<0.05$ was considered to be statistically significant. The analyses were done by means of the program R.

Results

FIG. 1 shows the distribution of the number of risk alleles in cases and controls (see also Table 11).

The same form of distribution is observed in both groups however, there is a displacement towards the right of the number of alleles in the cases (mean of risk alleles [typical deviation] 7,9 [1,8] in cases and 6,8 [1,8] in controls, value of $p=2\times10-16$). To determine whether the increase of risk was constant in the different groups defined by the number of alleles the magnitude of the risk for coronary heart disease was calculated in every group taking as reference the group with 7 alleles of risk. In FIG. 2 the OR and the regression coefficient ($\beta$) for each group with respect to the reference group, the change in the value of the regression coefficient ($\Delta\beta$) between consecutive categories, and the value of p given by the Fisher exact test for differences between cases and controls are shown. FIG. 1 shows a graphic representation of the regression coefficient obtained ($\beta$).

The increase of risk for increase of allele seems to be constant in the range of values observed. To quantify this increase per allele the variable number of alleles was considered as a continuous variable and it was estimated that the OR per increment in allele was 1,18 (confidence interval at 95%: 1,15-1,22; $p=2\times10^{-16}$); this linear model explains the 92% of the variability for the $\beta$ values obtained.

When these analyses were realized weighting each of the variants selected for the magnitude of their individual effect, the results were almost identical (OR for increase of allele=1,18; confidence interval at 95%: 1,14-1,21).

No statistically significant interaction was observed between the genetic variants, a result that also supports an additive effect of the analyzed variants.

Figure 3:
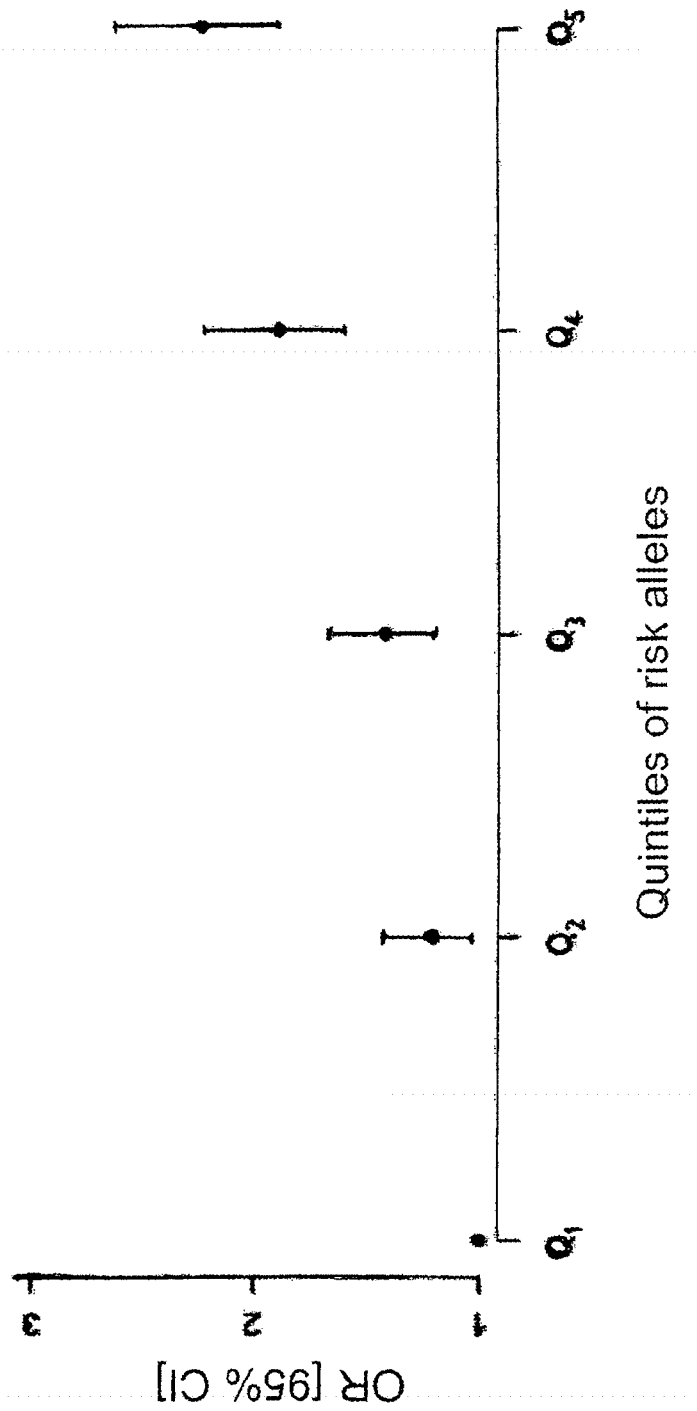

The results of the analysis defining 5 groups according to the quintiles of number of risk alleles and taking as reference the quintile with the lowest number of alleles are shown in FIG. 3. The increments in the risk ($\Delta\beta$) between the consecutive quintiles are similar (average increase of $\beta$: 0,198), and the OR observed between the ends is 2,21 (FIG. 4).

Conclusion

We have verified that the association between the number of risk alleles and the risk of coronary heart disease is linear and direct, so that to a higher number of risk alleles the probability of presenting coronary heart disease is higher. This linear association has been observed for other phenotypes like arterial blood pressure and diabetes.

The magnitude of the association observed, determined by the regression coefficient is similar to that observed in some classical cardiovascular risk factors included in the functions of coronary risk. For example, in the function of Framingham's risk and its adaptations, the difference in men between the regression coefficients of the ends for the variable cholesterol (<160 and ≥280 mg/dL) is 1,32 (that would correspond to an OR of 3,74) and for the variable blood pressure (ideal and degree II-III of hypertension) is 0,62 (OR=1,86). In our analysis the difference between the regression coefficient of the extreme categories of quintiles of number of alleles is 0,79, (OR=2,20) similar to the values of the arterial blood pressure; and considering the number of alleles and taking the group of 4 and 12 as ends of risk alleles the difference in the regression coefficients is 1,05 (OR=2, 86), slightly lower than that of cholesterol.

In conclusion, the results of this study show that this type of punctuation of genetic risk for coronary heart disease which is based on an additive effect of a number of risk alleles in different genetic markers that are independent from the classical cardiovascular risk factors, is associated with a higher coronary heart disease risk.

| Alleles | Number of controls | Number of cases | OR [95% CI] | β | Δβ | p value | |
|---|---|---|---|---|---|---|---|
| 1 | 0 | 1 | 3.13 [0.04-245.35] | 1.141 | 1.603 | $4 \times 10^{-01}$ | |
| 2 | 2 | 1 | 0.63 [0.01-5.62] | −0.462 | 0.192 | $1 \times 10^{-01}$ | |
| 3 | 24 | 8 | 0.52 [0.21-1.13] | −0.654 | −0.298 | $1 \times 10^{-01}$ | |
| 4 | 85 | 38 | 0.70 [0.47-1.01] | −0.356 | −0.042 | $5 \times 10^{-02}$ | |
| 5 | 269 | 127 | 0.74 [0.58-0.93] | −0.314 | −0.231 | $7 \times 10^{-03}$ | |
| 6 | 430 | 254 | 0.92 [0.77-1.11] | −0.083 | −0.083 | $4 \times 10^{-01}$ | |
| 7 | 592 | 379 | 1 | 0 | 0 | 1 | Reference group |
| 8 | 550 | 410 | 1.16 [0.99-1.37] | 0.148 | 0.148 | $7 \times 10^{-02}$ | |
| 9 | 395 | 389 | 1.54 [1.30-1.83] | 0.432 | 0.284 | $5 \times 10^{-07}$ | |
| 10 | 217 | 230 | 1.65 [1.35-2.02] | 0.501 | 0.069 | $7 \times 10^{-07}$ | |
| 11 | 80 | 107 | 2.09 [1.58-2.76] | 0.737 | 0.236 | $2 \times 10^{-07}$ | |
| 12 | 25 | 32 | 2.00 [1.22-3.23] | 0.693 | −0.044 | $4 \times 10^{-03}$ | |
| 13 | 4 | 11 | 4.30 [1.56-12.41] | 1.458 | 0.765 | $2 \times 10^{-02}$ | |
| 14 | 0 | 1 | 3.13 [0.04-245.35] | 1.141 | −0.317 | $4 \times 10^{-01}$ | |

The invention claimed is:

1. A method of detecting polymorphisms in a biological sample, comprising
   (a1) assaying the biological sample isolated from a human subject for the presence of polymorphisms at position 27 within each of the nucleic acid sequences of SEQ ID NO:1, SEQ ID NO:3, SEQ ID NO:7, SEQ ID NO:8, SEQ ID NO:9, and SEQ ID NO:10 by direct sequencing of nucleic acids in the sample;
   or
   (a2) assaying the biological sample isolated from a human subject for the presence of polymorphisms at position 27 within each of the nucleic acid sequences of SEQ ID NO:1, SEQ ID NO:3, SEQ ID NO:7, SEQ ID NO:8, SEQ ID NO:9, and SEQ ID NO:10 by detecting hybridization or lack of hybridization of the nucleic acid sequences of SEQ ID NO:1, SEQ ID NO:3, SEQ ID NO:7, SEQ ID NO:8, SEQ ID NO:9, and SEQ ID NO:10 in the biological sample with the set of nucleic acid probes; and
   (b) detecting polymorphisms in the biological sample at position 27 within the nucleic acid sequences of SEQ ID NO:1, SEQ ID NO:3, SEQ ID NO:7, SEQ ID NO:8, SEQ ID NO:9, and SEQ ID NO:10 based on the sequencing in (a1) or detecting hybridization or lack of hybridization in (a2);
   wherein the polymorphism at position 27 within the nucleic acid sequences of SEQ ID NOs:1, 3 and 7-10 is a C in SEQ ID NO:1, C in SEQ ID NO:3, T in SEQ ID NO:7, C in SEQ ID NO:8, C in SEQ ID NO:9, and T in SEQ ID NO:10.

2. The method according to claim 1, further comprising determining one or more of age, race, sex, body mass index, blood pressure, smoking status, low density lipoprotein (LDL)- or high density lipoprotein (HDL)-cholesterol level, systolic blood pressure, diastolic blood pressure, history of heart failure, diabetes, renal insufficiency, left ventricular hypertrophy, alcohol consumption history, smoking history, exercise history, diet, and family history of cardiovascular disease or disorder of the human subject.

3. The method according to claim 1, wherein the sample is an oral tissue sample, scraping, or wash, a biological fluid sample, saliva, urine or blood.

4. The method according to claim 1, further comprising amplifying nucleic acids in the sample, wherein the presence or absence of the polymorphisms is identified by amplifying or failing to amplify an amplification product from the sample, wherein the amplification product is preferably digested with a restriction enzyme before analysis and/or wherein the polymorphisms are identified by hybridizing the nucleic acid sample with a primer label which is a detectable moiety.

5. The method according to claim 1, wherein the method comprises assaying the biological sample for the presence of polymorphisms at position 27 within each of the nucleic acid sequences of SEQ ID NO:1 to 11.

6. The method according to claim 5, wherein said polymorphisms at said positions 27 are selected from the group of C in SEQ ID NO:1, A in SEQ ID NO:2, C in SEQ ID NO:3, T in SEQ ID NO:4, C in SEQ ID NO:5, A in SEQ ID NO:6, T in SEQ ID NO:7, C in SEQ ID NO:8, C in SEQ ID NO:9, T in SEQ ID NO:10 and T in SEQ ID NO:11.

\* \* \* \* \*